US007074416B2

(12) United States Patent
Dale

(10) Patent No.: US 7,074,416 B2
(45) **Date of Patent: *Jul. 11, 2006**

(54) ANTIGEN OF HYBRID M PROTEIN AND CARRIER FOR GROUP A STREPTOCOCCAL VACCINE

(75) Inventor: James B Dale, Memphis, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/141,627

(22) Filed: May 7, 2002

(65) Prior Publication Data

US 2002/0176863 A1 Nov. 28, 2002

Related U.S. Application Data

(63) Continuation of application No. 08/914,479, filed on Aug. 19, 1997, now Pat. No. 6,419,932, which is a continuation of application No. 08/409,270, filed on Mar. 23, 1995, now abandoned, which is a continuation of application No. 07/945,860, filed on Sep. 16, 1992, now abandoned.

(51) Int. Cl.

| | |
|---|---|
| ***A61K 39/09*** | (2006.01) |
| ***A61K 39/02*** | (2006.01) |
| ***A61K 39/00*** | (2006.01) |
| ***C07K 1/00*** | (2006.01) |
| ***C07K 2/00*** | (2006.01) |

(52) U.S. Cl. .............................. 424/244.1; 424/234.1; 424/190.1; 424/192.1; 424/184.1; 424/203.1; 424/237.1; 530/350; 530/300; 530/806; 530/825; 530/807; 514/2

(58) Field of Classification Search ................ 530/350, 530/300, 324–330, 825, 806, 807, 815; 424/234.1, 424/184.1, 237.1, 266.1, 190.1, 203.1, 192.1; 514/2

See application file for complete search history.

(56) References Cited

U.S. PATENT DOCUMENTS

| | | | | |
|---|---|---|---|---|
| 4,284,537 | A | 8/1981 | Beachey | 260/6 |
| 4,454,121 | A | 6/1984 | Beachey | 424/177 |
| 4,521,334 | A | 6/1985 | Beachey | 260/112.5 R |
| 4,597,967 | A | 7/1986 | Beachey | 424/88 |
| 4,705,684 | A | 11/1987 | Beachey | 424/88 |
| 4,886,663 | A * | 12/1989 | Houghten | 424/190.1 |
| 4,919,930 | A | 4/1990 | Beachey et al. | 424/88 |
| 5,124,153 | A | 6/1992 | Beachey et al. | 424/93 P |
| 5,149,657 | A * | 9/1992 | Maugh et al. | 435/320.1 |
| 5,182,109 | A | 1/1993 | Tamura et al. | 424/92 |
| 5,279,937 | A * | 1/1994 | Rowe | 435/6 |
| 5,306,492 | A * | 4/1994 | Porro | 424/88 |
| 5,763,733 | A | 6/1998 | Whitlow et al. | 530/387.3 |
| 6,063,386 | A | 5/2000 | Dale et al. | 424/244.1 |
| 6,072,036 | A * | 6/2000 | Marasco et al. | 530/387.3 |
| 6,419,932 | B1 * | 7/2002 | Dale | 424/244.1 |

FOREIGN PATENT DOCUMENTS

| | | | |
|---|---|---|---|
| EP | 0035384 | * | 9/1981 |
| WO | WO 91/02799 | * | 3/1991 |
| WO | WO 91/04036 | * | 4/1991 |

OTHER PUBLICATIONS

Newton et al. Infect. Immun. 59: 2158-2165, 1991.*

Beachey et al. J. Immunol. 136: 2287-2292, 1986b.*

The American Heritage Dictionary, Second College Edition, p. 805, 1976.*

Ada, G.L., *Fundamental Immunology*, 2nd Edition, William E. Paul (ed.), Raven Press Ltd., New York, 1989, Chapter 36, "Vaccines," pp. 1010-1011.

Baird et al., "Epitopes of Group A Streptococcal M Protein Shared With Antigens of Articular Cartilage and Synovium," *The Journal of Immunology* 146(9): 3132-3137, May 1, 1991.

Beall et al., "Sequencing *emm*-Specific PCR Products for Routine and Accurate Typing of Group A Streptococci," *Journal of Clinical Microbiology* 34(4): 953-958, Apr. 1996.

Beachey et al., "Peptic Digestion of Streptococcal M Protein II. Extraction of M Antigen from Group A Streptococci With Pepsin," *Infection and Immunity* 9(5): 891-896, May 1974.

Beachey et al., "Human Immune Response to Immunization with a Structurally Defined Polypeptide Fragment of Streptococcal M Protein," *J. Exp. Med.* 150: 862-877, Oct. 1979.

Beachey et al., "Opsonic Antibodies Evoked by Hybrid Peptide Copies of Types 5 and 24 Streptococcal M Proteins Synthesized in Tandem," *J. Exp. Med. 168*: 1451-1458, Jun. 1986.

Beachey et al., "Purification and Properties of M Protein Extracted From Group A Streptococci With Pepsin: Covalent Structure of the Amino Terminal Region of Type 24 M Antigen," *The Journal of Experimental Medicine 145*: 1469-1483, 1977.

Beachey et al., "Type-specific protective immunity evoked by synthetic peptide of *Streptococcus pyogenes* M protein," *Nature 292*: 457-459, Jul. 1981.

Beachey et al., "Repeating covalent structure of streptococcal M protein," *Proc. Natl. Acad. Sci. USA 75*(7): 3163-3167, Jul. 1978.

(Continued)

*Primary Examiner*—S. Devi
(74) *Attorney, Agent, or Firm*—Seed IP Law Group PLLC

(57) ABSTRACT

Recombinant hybrid streptococcal M protein antigens are provided which elicit protective antibodies against Group A streptococci and prevent rheumatic fever. Recombinant hybrid genes which encode the antigen are provided. Vaccine compositions and methods of administering the compositions are provided to elicit immunity against Group A streptococci.

30 Claims, 7 Drawing Sheets

OTHER PUBLICATIONS

Beachey et al., "Repeating Covalent Structure and Protective Immunogenicity of Native and Synthetic Polypeptide Fragments of Type 24 Streptococcal M Protein," *The Journal of Biological Chemistry* 258(21): 13250-13257, Nov. 10, 1983.
Beachey et al., "Primary Structure of Protective Antigens of Type 24 Streptococcal M Protein," *The Journal of Biological Chemistry* 255(13):6284-6289, Jul. 10, 1980.
Beachey et al., "Immunogenicity in Animals and Man of a Structurally Defined Polypeptide of Streptococcal M Protein," *Transactions of the Association of American Physicians* vol. XCII: 346-354, 1979.
Beachey et al., "Separation of the Type Specific M Protein From Toxic Gross Reactive Antigens of Group A Streptococci," *Transactions of the Association of American Physicians 90th Session* vol. XC: 390-400, 1977.
Beachey et al., "Protective Immunogenicity and T Lymphocyte Specificity of a Trivalent hybrid Peptide Containing $NH_2$- Terminal Sequences of Types 5, 6, and 24 M Proteins Synthesized in Tandem," *Journal of Experimental Medicine 166*: 647-656, Sep. 1987.
Beachey and Stollerman, "Toxic Effects of Streptococci M Protein on Platelets and Polymorphonuclear Leukocytes in Human Blood," *The Journal of Experimental Medicine 134*: 351-365, 1971.
Beachey and Stollerman, "Mediation of Cytotoxic Effects of Streptococcal M Protein by Nontype-Specific Antibody in Human Sera," *The Journal of Clinical Investigation 52*: 2563-2570, Oct. 1973.
Beachey and Seyer, "Protective and Nonprotective Epitopes of Chemically Synthesized Peptides of the $NH_2$-Terminal Region of Type 6 Streptococcal M Protein," *The Journal of Immunology 136*(6):2287-2292, Mar. 15, 1986.
Beachey and Seyer, *Seminars in Infectious Disease. vol. IV Bacterial Vaccines*, Thieme-Stratton Inc., New York, New York, 1982, Chapter 57, "Primary Structure and Immunochemistry of Group A Streptococcal M. Proteins," pp. 401-410.
Beachey and Ofek, "Epithelial Cell Binding of Group A Streptococci by Lipoteichoic Acid on Fimbriae Denuded of M Protein," *The Journal of Experimental Medicine 143*: 759-771, 1976.
Blenden et al., "Growth of *Listeria monocytogenes* in a Corn Silage Extract Medium," *Am. J. Vet. Res*. 29(11): 2237-2242, Nov. 1968.
Bricas et al., *Peptides*, Beyerman et al. (eds.), North-Holland Publishing Company, Amsterdam, 1967, "Structure et Synthese de la Subunite Peptidique de la Paroi de Trois Bacteries Gram-Positif," pp. 286-292 (+ *Biological Abstracts 50*(4): Abstract No. 20361, 1936).
Bronze et al., "Protective and Heart-Crossreactive Epitopes Located Within the $NH_2$ Terminus of Type 19 Streptococcal M Protein," *J. Exp. Med . 167*(6): 1849-1859, Jun. 1, 1988.
Chou and Fasman, "Prediction of Protein Conformation," *Biochemistry* 13(2): 222-245, 1974.
Clements, J.D., "Construction of a Nontoxic Fusion Peptide for Immunization against *Escherichia coli* Strains That Produce Heat-Labile and Heat-Stable Enterotoxins," *Infection and Immunity* 58: 1159-1166, 1990.
Cunningham and Beachey, "Peptic Digestion of Streptococcal M Protein I. Effect of Digestion at Suboptimal pH upon the Biological and Immunochemical Properties of Purified M Protein Extracts," *Infection and Immunity 9*(2): 244-248, Feb. 1974.
Cunningham et al., "Human and Murine Antibodies Cross-Reactive With Streptococcal M Protein and Myosin Recognize the Sequence Gln-Lys-Ser-Lys-Gln in M Protein," *The Journal of Immunology 143*(8): 2677-2683, Oct. 15, 1989.
Dale, J.B., "Multivalent group A streptococcal vaccine designed to optimize the immunogenicity of six tandem M protein fragments," *Vaccine 17*: 193-200, 1999.
Dale, J.B., "Group A Streptococcal Vaccines," *New Vaccines and New Vaccine Technology* 13(1): 227-243, Mar. 1999.
Dale, J.B., "Group A Steptococcal Vaccines." *Pediatric Annals 27*(5): 301-308, May 1998.
Dale and Beachey, "Multiple, Heart-Cross-Reactive Epitopes of Streptococcal M Proteins," *Journal of Experimental Medicine 161*: 113-122, Jan. 1985.
Dale and Beachey, "Localization of Protective Epitopes of the Amino Terminus of Type 5 Streptococcal M Protein," *Journal of Experimental Medicine* 163: 1191-1202, May 1986.
Dale and Beachey, "Epitopes of Streptococcal M Proteins Shared With Cardiac Myosin," *Journal of Experimental Medicine 162*: 583-591, Aug. 1985.
Dale and Beachey, "Sequence of Myosin-Crossreactive Epitopes of Streptococcal M Protein," *Journal of Experimental Medicine 164*: 1785-1790, Nov. 1986.
Dale et al., "Blastogenic Responses of Human Lymphocytes to Structurally Defined Polypeptide Fragments of Streptococcal M Protein," *The Journal of Immunology 126*(4): 1499-1505, Apr. 1981.
Dale et al., "Heterogeneity of Type-Specific and Cross-Reactive Antigenic Determinants Within a Single M Protein of Group A Streptococci," *The Journal of Experimental Medicine 151*: 1026-1083, 1980.
Dale et al., "Type-Specific Immunogenicity of a Chemically Synthesized Peptide Fragment of Type 5 Streptococcal M Protein," *Journal of Experimental Medicine 158*: 1727-1732, Nov. 1983.
Dale et al., "New protective antigen of group A streptococci," *The Journal of Clinical Investigation* 103(9): 1261-1268, May 1999.
Dale et al., "Recombinant, octavalent group A streptococcal M protein vaccine," *Vaccine* 14(10): 944-948, 1996.
Dale et al., "Hyaluronate Capsule and Surface M Protein in Resistance to Opsonization of Group A Streptococci," *Infection and Immunity* 64(5): 1495-1501, May 1996.
Dale et al., "Recombinant Tetravalent Group A Streptococcal M Protein Vaccine," *The Journal of Immunology* 151(4): 2188-2194, Aug. 15, 1993.
Dixit et al., "Covalent Structure of Collagen: Amino Acid Sequence of $\alpha$1-CB6A of Chick Skin Collagen," *Biochemistry 14*(9): 1933-1938, 1975.
Edman and Begg, "A Protein Sequenator," *European J. Biochem . 1*: 80-91, 1967.
Fischetti, V.A., "Streptococcal M Protein," *Scientific American 264*(6): 58-65, Jun. 1991.
Fischetti et al., *New Perspectives on Streptococci and Streptococcal Infections. Proceedings of the XI Lancefield International Symposium on Streptococci and Streptococcal Disease*, Sienna, Italy, Sep. 10-14, 1990, Gustav Fischer Verlag, Stuttgart, Jena, New York, 1992, "Surface Proteins from Gram-Positive Cocci Share Unique Structural Features," pp. 165-167.
Freimer and McCarty, "Rheumatic Fever," *Scientific American 213*(6): 67-74, 1965.
Gibbons et al., "Studies of Individual Amino Acid Residues of the Decapepetide Tyrocidine A by Proton Double-Resonance Difference Spectroscopy in the Correlation Mode," *Biochemistry 14*(2): 420-429, 1975.
Goldberg et al., "Serological Demonstration of H-Y (Male) Antigen on Mouse Sperm," *Nature 232*: 478-780, Aug. 13, 1971.
Hollingshead et al., "Complete Nucleotide Sequence of Type 6 M Protein of the Group A *Streptococcus*," *The Journal of Biological Chemistry 261*(4): 1677-1686, Feb. 5, 1986.
Hopp and Woods, "Prediction of protein antigenic determinants from amino acid sequences," *Proc. Natl. Acad. Sci. USA 78*(6): 3824-3828, Jun. 1981.
Jones et al., "Differential Effects of Antibodies to Lyt-2 and L3T4 on Cytolysis by Cloned, Ia-Restricted T Cells Expressing Both Proteins," *The Journal of Immunology 139*(2): 380-384, Jul. 15, 1987.
Kang, A.H., "Studies on the Location of Intermolecular Cross-Links in Collagen. Isolation of a CNBr Peptide Containing δ-Hydroxylysinonorleucine," *Biochemistry 11*(10): 1828-1835, 1972.
Kang and Gross, "Amino Acid Sequence of Cyanogen Bromide Peptides from the Amino-Terminal Region of Chick Skin Collagen," *Biochemistry 9*(4): 796-804, Feb. 17, 1970.
Kaplan et al., "Concise Communications," *The Journal of Infectious Diseases 159*(1): 101-103, Jan. 1989.
Koch et al., "Purification and Structural Analysis of Streptolysin S (SLS)," *Federation Proceedings 42*(7): 1810, Abstract No. 309, 1983.
Kraus et al., "Identification of an Epitope of Type 1 Streptococcal M Protein That is Shared With a 43-kDa Protein of Human Myocardium and Renal Glomeruli," *The Journal of Immunology 145*(12): 4089-4093, Dec. 15, 1990.
Kraus et al., "Sequence and Type-Specific Immunogenicity of the Amino-Terminal Region of Type 1 Streptococcal M Protein," *The Journal of Immunology 139*(9): 3084-3090, Nov. 1, 1987.
Lancefield, R.C., "Peristence of Type-Specific Antibodies in Man Following Infection With Group A Streptococci," *J. Exp. Med . 110*(1): 271-292, 1959.
Laver et al., "Antigenic drift in type A influenza virus: Peptide mapping and antigenic analysis of A/PR/8/34 (HON1) variants selected with monoclonal antibodies," *Proc. Natl. Acad. Sci. USA 76*(3): 1425-1429, Mar. 1979.
Lockey, R.F., "Urticaria of Unknown Origin," *Hospital Practice* 14(4): 49-54, Apr. 1979.
Manjula and Fishcetti, "Tropomyosin-Like Seven Residue Periodicity in Three Immunologically Distinct Streptococcal M Proteins and its Implications for the Antiphagocytic Property of the Molecule," *J. Exp. Med . 151*: 695-708, Mar. 1980.
Miller et al., "Conservation of Protective and Nonproductive Epitopes in M Proteins of Group A Streptococci," *Infection and Immunity 56*(8): 2198-2204, Aug. 1988.
Mouw et al., "Molecular Evolution of Streptococcal M Protein: Cloning and Nucleotide Sequence of the Type 24 M Protein Gene and Relation to Other Genes of *Streptococcus pyogenes*," *Journal of Bacteriology 70*(2): 676-684, Feb. 1988.
Phillips Jr., et al., "Streptococcal M protein: α-Helical coiled-coil structure and arrangement on the cell surface," *Proc. Natl. Acad. Sci. USA 78*(8): 4689-4693, Aug. 1981.
Podbielski et al., "Application of the polymerase chain reaction to study the M protein(-like) gene family in beta-hemolytic streptococci," *Med. Microbiol. Immunol . 180*: 213-227, 1991.
Rijn et al., "Group A Streptococcal Antigens Cross-Reactive With Myocardium," *The Journal of Experimental Medicine 146*: 579-599, 1977.
Robbins et al., "*Streptococcus pyogenes* Type 12 M Protein Gene Regulation by Upstream Sequences," *Journal of Bacteriology 169*(12): 5633-5640, Dec. 1987.
Sargent et al., "Sequence of Protective Epitopes of Streptococcal M Proteins Shared With Cardiac Sarcolemmal Membranes," *The Journal of Immunology 139*(4): 1285-1290, Aug. 15, 1987.
Seyer and Kang, "Covalent Structure of Collagen: Amino Acid Sequence of Cyanogen Bromide Peptides from the Amino-Terminal Segment of Type III Collagen of Human Liver," *Biochemistry 16*(6): 1040-1065, 1977.
Seyer et al., "Primary Structural Similarities Between Types 5 and 24 M Proteins of *Streptococcus pyogenes*," *Biochemical and Biophysical Research Communications 92*(2): 546-553, Jan. 29, 1980.
Smithies et al., "Quantitative Procedures for Use with the Edman-Begg Sequenator. Partial Sequences of Two Unusual Immunoglobulin Light Chains, Rzf and Sac," *Biochemistry 10*(26): 4912-4921, 1971.
Vashishtha et al., "Reactivity of Antisera to Peptides Corresponding to the C-repeat Region of Streptococcal M Protein with Mammalian Coiled-Coil Proteins," *Abstracts of the 91st General Meeting of the Society for Microbiology* 1991: 129, Abstract No. E-66, 1991.
Weigent et al., "Induction of Human Gamma Interferon by Structurally Defined Polypeptide Fragments of Group A Streptococcal M Protein," *Infection and Immunity 43*(1): 122-126, Jan. 1984.
Wistedt et al., "Identification of a plasminogen-binding motif in PAM, a bacterial surface protein," *Molecular Microbiology 18*(3): 569-578, 1995.
Wittner and Fox, "Homologous and Heterologous Protection of Mice with Group A Streptococcal M Protein Vaccines," *Infection and Immunity 15*(1): 104-108, Jan. 1977.

* cited by examiner

```
ATG AAT AAA GTA AAA TGT TAT GTT TTA TTT ACG GCG TTA CTA TCC TCT    48
Met Asn Lys Val Lys Cys Tyr Val Leu Phe Thr Ala Leu Leu Ser Ser

CTA TGT GCA TAC GGA GCT CCC CAG TCT ATT ACA GAA CTA TGT TCG GAA    96
Leu Cys Ala Tyr Gly Ala Pro Gln Ser Ile Thr Glu Leu Cys Ser Glu

TAT CGC AAC ACA CAA ATA TAT ACG ATA AAT GAC AAG ATA CTA TCA TAT   144
Tyr Arg Asn Thr Gln Ile Tyr Thr Ile Asn Asp Lys Ile Leu Ser Tyr

ACG GAA TCG ATG GCA GGC AAA AGA GAA ATG GTT ATC ATT ACA TTT AAG   192
Thr Glu Ser Met Ala Gly Lys Arg Glu Met Val Ile Ile Thr Phe Lys

AGC GGC GCA ACA TTT CAG GTC GAA GTC CCG GGC AGT CAA CAT ATA GAC   240
Ser Gly Ala Thr Phe Gln Val Glu Val Pro Gly Ser Gln His Ile Asp

TCC CAA AAA AAA GCC ATT GAA AGG ATG AAG GAC ACA TTA AGA ATC ACA   288
Ser Gln Lys Lys Ala Ile Glu Arg Met Lys Asp Thr Leu Arg Ile Thr

TAT CTG ACC GAG ACC AAA ATT GAT AAA TTA TGT GTA TGG AAT AAT AAA   336
Tyr Leu Thr Glu Thr Lys Ile Asp Lys Leu Cys Val Trp Asn Asn Lys
                                                 NcoI
ACC CCC AAT TCA ATT GCG GCA ATC AGT ATG GAA AAC CAT GGA GTC GCG   384
Thr Pro Asn Ser Ile Ala Ala Ile Ser Met Glu Asn His Gly Val Ala

ACT AGG TCT CAG ACA GAT ACT CTG GAA AAA TAA                       417
Thr Arg Ser Gln Thr Asp Thr Leu Glu Lys
     M24
```

*Fig. 1*

ATG GTC GCG ACT AGG TCT CAG ACA GAT ACT CTG GAA AAA GTA CAA GAA 48
Met Val Ala Thr Arg Ser Gln Thr Asp Thr Leu Glu Lys Val Gln Glu
M5 →

GGA TCC AAC AAA ATT TCA GAC GCA AGC CGT AAG GGT CTT CGT CGT GAC 96
Gly Ser Asn Lys Ile Ser Asp Ala Ser Arg Lys Gly Leu Arg Arg Asp
Bam H1 M5 COOH-TERM HALF

TTA GAC GCA TCG CGT GAA GCT AAG AAG CAA TTA GAA GCT GAA CAC CAA 144
Leu Asp Ala Ser Arg Glu Ala Lys Lys Gln Leu Glu Ala Glu His Gln

AAA CTT GAA GAA CAA AAC AAG ATT TCA GAA GCA AGT CGC AAA GGC CTT 192
Lys Leu Glu Glu Gln Asn Lys Ile Ser Glu Ala Ser Arg Lys Gly Leu

CGC CGT GAT TTA GAC GCA TCA CGT GAA GCT AAG AAG CAA TTA GAA GCT 240
Arg Arg Asp Leu Asp Ala Ser Arg Glu Ala Lys Lys Gln Leu Glu Ala

GAA CAA CAA AAA CTT GAA GAA CAA AAC AAG ATT TCA GAA GCA AGT CGC 288
Glu Gln Gln Lys Leu Glu Glu Gln Asn Lys Ile Ser Glu Ala Ser Arg

AAA GGC CTT CGC CGT GAT TTA GAC GCA TCA CGT GAA GCT AAG AAA CAA 336
Lys Gly Leu Arg Arg Asp Leu Asp Ala Ser Arg Glu Ala Lys Lys Gln

GTT GAA AAA GCT TTA GAA GAA GCA AAC AGC AAA TTA GCT GCT CTT GAA 384
Val Glu Lys Ala Leu Glu Glu Ala Asn Ser Lys Leu Ala Ala Leu Glu

AAA CTT AAC AAA GAG CTT GAA GAA AGC AAG AAA TTA ACA GAA AAA GAA 432
Lys Leu Asn Lys Glu Leu Glu Glu Ser Lys Lys Leu Thr Glu Lys Glu

AAA GCT GAG CTA CAA GCA AAA CTT GAA GCA GAA GCA AAA GCA CTC AAA 480
Lys Ala Glu Leu Gln Ala Lys Leu Glu Ala Glu Ala Lys Ala Leu Lys

GAA CAA TTA GCA AAA CAA GCT GAA GAA CTT GCA AAA CTA AGA GCT GGA 528
Glu Gln Leu Ala Lys Gln Ala Glu Glu Leu Ala Lys Leu Arg Ala Gly

AAA GCA TCA GAC TCA CAA ACC CCT GAT ACA AAA CCA GGA AAC AAA GCT 576
Lys Ala Ser Asp Ser Gln Thr Pro Asp Thr Lys Pro Gly Asn Lys Ala

GTT CCA GGT AAA GGT CAA GCA CCA CAA GCA GGT ACA AAA CCA AAC CAA 624
Val Pro Gly Lys Gly Gln Ala Pro Gln Ala Gly Thr Lys Pro Asn Gln

*Fig. 4A*

```
AAC AAA GCA CCA ATG AAG GAA ACT AAG AGA CAG TTA CCA TCA ACA GGT      672
Asn Lys Ala Pro Met Lys Glu Thr Lys Arg Gln Leu Pro Ser Thr Gly

GAA ACA GCT AAC CCA TTC TTC ACA GCG GCA GCC CTT ACT GTT ATG GCA      720
Glu Thr Ala Asn Pro Phe Phe Thr Ala Ala Ala Leu Thr Val Met Ala

ACA GCT GGA GTA GCA GCA GTT GTA AAA CGC AAA GAA GAA AAT TAA          765
Thr Ala Gly Val Ala Ala Val Val Lys Arg Lys Glu Glu Asn
```

*Fig. 4B*

```
ATG GTC GCG ACT AGG TCT CAG ACA GAT ACT CTG GAA AAA GTA CAA GAA      48
Met Val Ala Thr Arg Ser Gln Thr Asp Thr Leu Glu Lys Val Gln Glu
   M5(A) ------------------------------------------------------->

GTC GCG ACT AGG TCT CAG ACA GAT ACT CTG GAA AAA GTA CAA GAA GTC      96
Val Ala Thr Arg Ser Gln Thr Asp Thr Leu Glu Lys Val Gln Glu Val
   M5(B) ----------------------------------------------------> M5(C)

GCG ACT AGG TCT CAG ACA GAT ACT CTG GAA AAA GTA CAA GAA GGA TTC     144
Ala Thr Arg Ser Gln Thr Asp Thr Leu Glu Lys Val Gln Glu Gly Phe
----------------------------------------------------------> Bam H1

AAC AAA ATT TCA GAC GCA AGC CGT AAG GGT CTT CGT CGT GAC TTA GAC     192
Asn Lys Ile Ser Asp Ala Ser Arg Lys Gly Leu Arg Arg Asp Leu Asp
M5      COOH-TERM HALF ----------------------->|

GCA TCG CGT GAA GCT AAG AAG CAA TTA GAA GCT GAA CAC CAA AAA CCT     240
Ala Ser Arg Glu Ala Lys Lys Gln Leu Glu Ala Glu His Gln Lys Pro

GAA GAA CAA AAC AAG ATT TCA GAA GCA AGT CGC AAA GGC CTT CGC CGT     288
Glu Glu Gln Asn Lys Ile Ser Glu Ala Ser Arg Lys Gly Leu Arg Arg

GAT TTA GAC GCA TCA CGT GAA GCT AAG AAG CAA TTA GAA GCT GAA CAA     336
Asp Leu Asp Ala Ser Arg Glu Ala Lys Lys Gln Leu Glu Ala Glu Gln

CAA AAA CTT GAA GAA CAA AAC AAG ATT TCA GAA GCA AGT CGC AAA GGC     384
Gln Lys Leu Glu Glu Gln Asn Lys Ile Ser Glu Ala Ser Arg Lys Gly

CTT CGC CGT GAT TTA GAC GCA TCA CGT GAA GCT AAG AAA CAA GTT GAA     432
Leu Arg Arg Asp Leu Asp Ala Ser Arg Glu Ala Lys Lys Gln Val Gly

AAA GCT TTA GAA GAA GCA AAC AGC AAA TTA GCT GCT CTT GAA AAA CTT     480
Lys Ala Leu Glu Glu Ala Asn Ser Lys Leu Ala Ala Leu Glu Lys Leu

AAC AAA GAG CTT GAA GAA AGC AAG AAA TTA ACA GAA AAA GAA AAA GCT     528
Asn Lys Glu Leu Glu Glu Ser Lys Lys Leu Thr Glu Lys Glu Lys Ala

GAG CTA CAA GCA AAA CTT GAA GCA GAA GCA AAA GCA CTC AAA GAA CAA     576
Glu Leu Gln Ala Lys Leu Glu Ala Glu Ala Lys Ala Leu Lys Glu Gln

TTA GCA AAA CAA GCT GAA GAA CTT GCA AAA CTA AGA GCT GGA AAA GCA     624
Leu Ala Lys Gln Ala Glu Glu Leu Ala Lys Leu Arg Ala Gly Lys Ala
```

*Fig. 5A*

TCA GAC TCA CAA ACC CCT GAT ACA AAA CCA GGA AAC AAA GCT GTT CCA 720
Ser Asp Ser Gln Thr Pro Asp Thr Lys Pro Gly Asn Lys Ala Val Pro

GGT AAA GCT CAA GCA CCA CAA GCA GGT ACA AAA CCA AAC CAA AAC AAA 768
Gly Lys Ala Gln Ala Pro Gln Ala Gly Thr Lys Pro Asn Gln Asn Lys

GCA CCA ATG AAG GAA ACT AAG AGA CAG TTA CCA TCA ACA GGT GAA ACA 816
Ala Pro Met Lys Glu Thr Lys Arg Gln Leu Pro Ser Thr Gly Glu Thr

GCT AAC CCA TTC TTC ACA GCG GCA GCC CTT ACT GTT ATG GCA ACA GCT 816
Ala Asn Pro Phe Phe Thr Ala Ala Ala Leu Thr Val Met Ala Thr Ala

GGA GTA GCA GCA GTT GTA AAA CGC AAA GAA GAA AAT TAA 855
Gly Val Ala Ala Val Val Lys Arg Lys Glu Glu Asn

*Fig. 5B*

ANTIGEN OF HYBRID M PROTEIN AND CARRIER FOR GROUP A STREPTOCOCCAL VACCINE

CROSS-REFERENCE TO RELATED APPLICATIONS

This application is a continuation of U.S. patent application Ser. No. 08/914,479, filed Aug. 19, 1997, now U.S. Pat. No. 6,419,932; which is a continuation of U.S. patent application Ser. No. 08/409,270, filed Mar. 23, 1995, now abandoned; which is a continuation of U.S. patent application Ser. No. 07/945,860, filed Sep. 16, 1992, now abandoned. These applications are incorporated herein by reference in their entireties.

FIELD OF INVENTION

The present invention relates broadly to the field of recombinant vaccines. The vaccines are directed to preventing Group A streptococcal infections, which may otherwise result in rheumatic fever.

BACKGROUND OF THE INVENTION

Acute rheumatic fever (ARF) is the major cause of heart disease in children around the world. The disease is rampant in developing countries where prevalence rates of rheumatic heart disease may be as high as 35–40 per thousand individuals. By one estimate, it affects nearly six million school-age children in India. Although the incidence of ARF in the United States and other Western countries declined markedly during the later half of the twentieth century, there has been a remarkable resurgence of the disease in the United States.

Streptococci are a group of bacteria with the capacity to grow in chains. Many varieties are part of the normal bacterial flora in humans and are not especially harmful. However, a particular subgroup of streptococcal bacteria, called Group A and represented by *Streptococcus pyogenes*, is a human pathogen. Between 20 and 30 million cases of Group A streptococcal infections occur every year in the United States alone. These cases include infections of the skin and throat, forms of pneumonia and a recently identified disease resembling toxic shock. The most common infection is acute streptococcal pharyngitis, or strep throat, which occurs predominantly in school-age children. Strep throat qualifies as a major worldwide health problem if judged only by time lost from school and work and by the amount spent on related doctor's fees.

Strep throat's toll is much greater, however. In as many as 4% of the pharyngitis cases that are untreated or treated ineffectively, the strep infection leads to ARF. Current attempts to prevent ARF rely on treatment of the pharyngitis with antibiotics. During a recent outbreak of ARF in Utah, only a fourth of the patients sought health care prior to the onset of symptoms, and only a third recalled a recent sore throat. The finding that ARF may follow a subclinical infection in such a high percentage of individuals and the fact that access to health care in developing countries is not widely available serve to underscore the need for a safe and effective vaccine against Group A streptococci.

The causal relationship between streptococcal pharyngitis and ARF was established over 50 years ago, yet the mechanism of the pathogenesis of the disease remains unclear. It is widely held that ARF is an autoimmune disease, and that in the susceptible host the infection triggers an immune response that leads to inflammatory and sometimes destructive changes in target tissues. Streptococci have been shown to contain antigens that are immunologically cross-reactive with host tissues and heart cross-reactive antibodies from patients with rheumatic fever have been shown to react with streptococci. However, it was also shown that sera from patients with uncomplicated pharyngitis also may contain heart cross-reactive antibodies, yet these patients do not develop clinical evidence of carditis. Until the significance of tissue cross-reactive antibodies in the pathogenesis of ARF is better understood, there remains a need to exclude potentially harmful epitopes from vaccine preparations.

The surface M protein of Group A streptococci is the major virulence factor and protective antigen of these organisms. Group A streptococci have developed a system for avoiding some of the antimicrobial defenses of a human host. Strains of streptococci that are rich in M protein evade phagocytosis by PMNs and multiply in non-immune blood. Yet, resistance to an infection by these bacteria is possible if the host's body can produce opsonic antibodies directed against the M protein. Such antibodies will neutralize the protective capacity of the M protein and allow the *streptococcus* to be engulfed and destroyed by phagocytes. The development of secretory or mucosal immunity is also now suspected of playing an important role in preventing streptococcal infections.

A major obstacle to effective vaccine development has been the tremendous number of M protein serotypes (now over 80). Laboratory tests suggest that antibodies against one serotype do not offer protection against others. Immunity then appears to be type or sero-specific and optimal vaccines would require that most of the serotypes be represented, There is evidence that not all serotypes of Group A streptococci have the same potential to trigger acute rheumatic fever in susceptible individuals. The concept of "rheumatogenic" and "non-rheumatogenic" organisms is supported by multiple surveillance studies over many years and in diverse areas of the world. Thus, there are probably about 12–15 serotypes responsible for most cases of ARF. Some of these are types 1, 3, 5, 6, 14, 18, 19, 24, 27 and 29.

Previous studies have shown that in many cases the protective epitopes of M protein may be separated from the potentially harmful, autoimmune epitopes of the molecule. The $NH_2$-terminal segments of M proteins have evoked antibodies with the greatest bactericidal activity.

Previous studies have also shown that synthetic peptides copying limited regions of types 5, 6 and 24 M proteins evoked type-specific, opsonic antibodies that were not heart tissue cross-reactive. Because of their lack of immunogenicity (haptens), the synthetic peptides were chemically linked covalently to carrier proteins. However, such fragments of M proteins linked to carrier proteins with chemical reagents do not result in hybrid proteins of defined structures. Thus, in general it has not been possible to obtain antigens which can elicit specific, desired antibodies or which decrease the risk of undesirable side reactions. Further, formation of hapten—carrier complexes using chemical cross-linking reagents is time-consuming and costly and results in undefined heterogeneous mixtures of vaccine components.

It is evident from this description of the state of the art that there is an important need for a vaccine which is effective by raising sero-specific antibodies against the various serotypes of Group A streptococci, especially those serotypes capable of triggering acute rheumatic fever, which is known to follow a sore throat, without eliciting cross-reaction with human tissue. Particularly, there is an important need for a vaccine which has not only these properties, but which also is capable of raising protective antibodies to prevent sore throat, skin infections, deep tissue infections and streptococcal infections of the like that are not necessarily followed by rheumatic fever. The invention contributes to solving these important needs in human health.

SUMMARY OF THE INVENTION

The parent patent application is related to and was co-filed on the same day as patent application Ser. No. 07/945,954, entitled "RECOMBINANT MULTIVALENT M PROTEIN VACCINE" with named inventors James B. Dale and James W. Lederer.

The present invention provides recombinant M protein antigens. The antigens are constructed by recombinant DNA methods. They are comprised of amino acid fragments of serotypes of M protein, which fragments carry one or more epitopes that evoke opsonic antibodies against specific serotypes of Group A *streptoccocus* and, if desired, when the fragments carry appropriate epitopes, also evoke protective antibodies. The fragments are either fused directly or linked in tandem by an amino acid linker to an appropriate carrier. The antigens are generally non-immunogenic (or not adequately immunogenic) because of their molecular size or for other reasons.

The invention thus provides a recombinant fusion antigen comprising a gene encoding the carrier protein and an $NH_2$ or COOH-terminal M protein fragment carrying one or more epitopes. The recombinant antigen does not elicit antibodies which cross react with human heart or other human tissue.

In accordance with the invention, there are provided mixtures of antigens which are serotype-specific comprising the same or different carrier. Such a mixture of selected antigens-carriers or "cocktail" provides immunogenicity against several serotypes (and if desired raise different protective antibodies). The recombinant fusion antigens are constituted of segments of the $NH_2$ terminal portions of the M proteins, which fragments raise specific opsonic antibodies. Fusion antigens are also provided which are constituted of the COOH-terminal fragments of the M proteins. The COOH-terminal fragments raise protective antibodies of the mucosal or secretory type. In the antigen with an amino acid linker, the carrier and the fragment of the M protein, which carries the desired epitope, are linked in tandem by an amino acid linker, described in greater detail hereinafter, which has the capacity to promote the conformation of the fragment of the M protein to optimize the exposure of the epitope and thus to optimally raise the desired antibodies.

The invention also provides for an antigen comprised of a carrier, which constitutes the carboxy-terminal portion of a serotype of M protein linked by a linker or fused directly to an amino acid fragment of M protein. The carrier and fragment may be of the same or different serotype.

The invention also provides for carriers which are free of epitopes which elicit antibodies to serotypes of streptococcal M protein.

The invention provides recombinant hybrid genes which nucleotide sequences encode for the antigens of the present invention and a method of construction of such genes.

The invention further provides the new fusion genes or DNA fragments which code for the hybrid antigens and the transformed microorganisms (eukaryotes or prokaryotes) that express the hybrid antigens.

The invention also provides avirulent microorganisms which are transformed with the genes of the present invention. These microorganisms are especially suitable for oral administration to and immunization of mammals, in particular humans.

The invention provides for methods of administration of the antigens of the present invention in therapeutic compositions via oral, intranasal and parenteral routes of administration, to induce or evoke opsonic and/or protective antibodies against serotypes of Group A *streptoccocus*. The administered compositions confer immunity to immunized mammals against Group A streptococci.

The invention provides vaccine compositions which are comprised of the antigens of the present invention and biologically acceptable diluents for administration to and immunization of mammals, in particular humans. The composition is administrable orally, whereby the antigens are released from the transformed microorganism and the desired antibodies are elicited, intranasally and parenterally.

The invention also provides for broad spectrum protection and wide-ranging immunity against all serotypes of Group A streptococci, particularly rheumatogenic streptococci by the formulation of compositions of the antigens, either singly or in mixtures or "cocktails".

BRIEF DESCRIPTION OF THE FIGURES

FIG. 1 shows the DNA (SEQ ID NO:1) and deduced protein sequence (SEQ ID NO:2) of LT-B-M24 hybrid molecule.

FIGS. 4A and 4B show the order of the nucleotides (SEQ ID NO:3) and amino acid residues (SEQ ID NO:4) of an antigen of a fragment of M5 and a carrier of the carboxy-terminal portion of M5.

FIGS. 5A and 5B show the order of the nucleotides (SEQ ID NO:5) and amino acid residues (SEQ ID NO:6) of an antigen of fragments of M5 and a carrier of the carboxy-terminal portion of M5.

DETAILED DESCRIPTION OF THE FIGURES

The present invention and many of the attendant advantages of the invention will be better understood upon a reading of the following detailed description when considered in connection with the accompanying drawings wherein:

FIG. 1 shows the DNA (SEQ ID NO:1) and deduced protein sequence (SEQ ID NO:2) of LT-B-M24 hybrid molecule. The sequence of the fusion gene was confirmed from base 228 to the 3' end. The remainder of the LT-B sequence is from Clements (16). The NcoI site linking the LT-B and M24 components is indicated. The M24 subunit is underlined.

Figure 2:
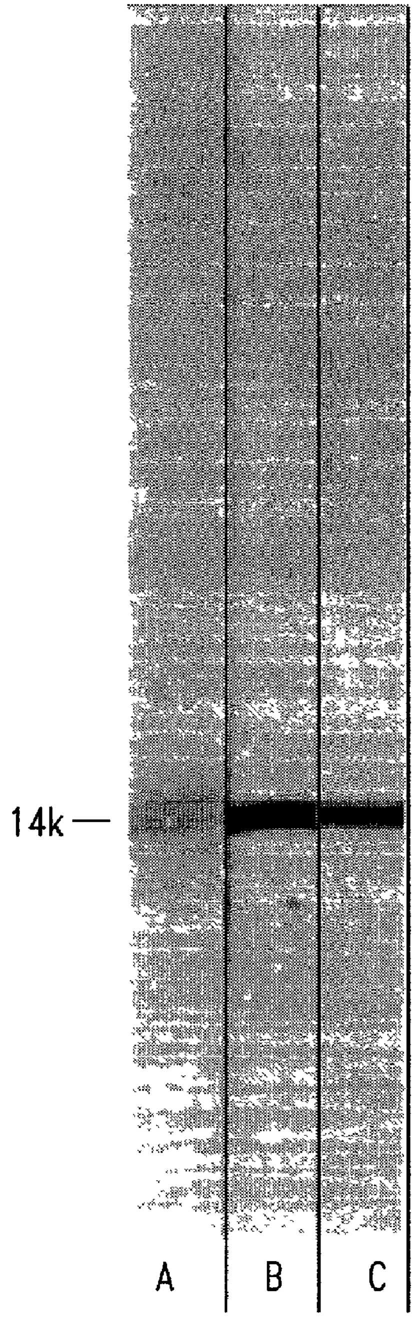
FIG. 2 shows the immunoblot analysis of purified LT-B-M24 hybrid protein.

FIG. 2 shows the immunoblot analysis of purified LT-B-M24 hybrid protein. The purified protein was electrophoresed on an SDS-polyacrylamide gel and transferred to nitrocellulose paper. Coomassie blue stained a single band with an apparent molecular weight of 14 kDa (lane A). The purified protein reacted with rabbit antisera against LT-B (lane B) and SM24 (1–29)C (lane C).

Figure 3:
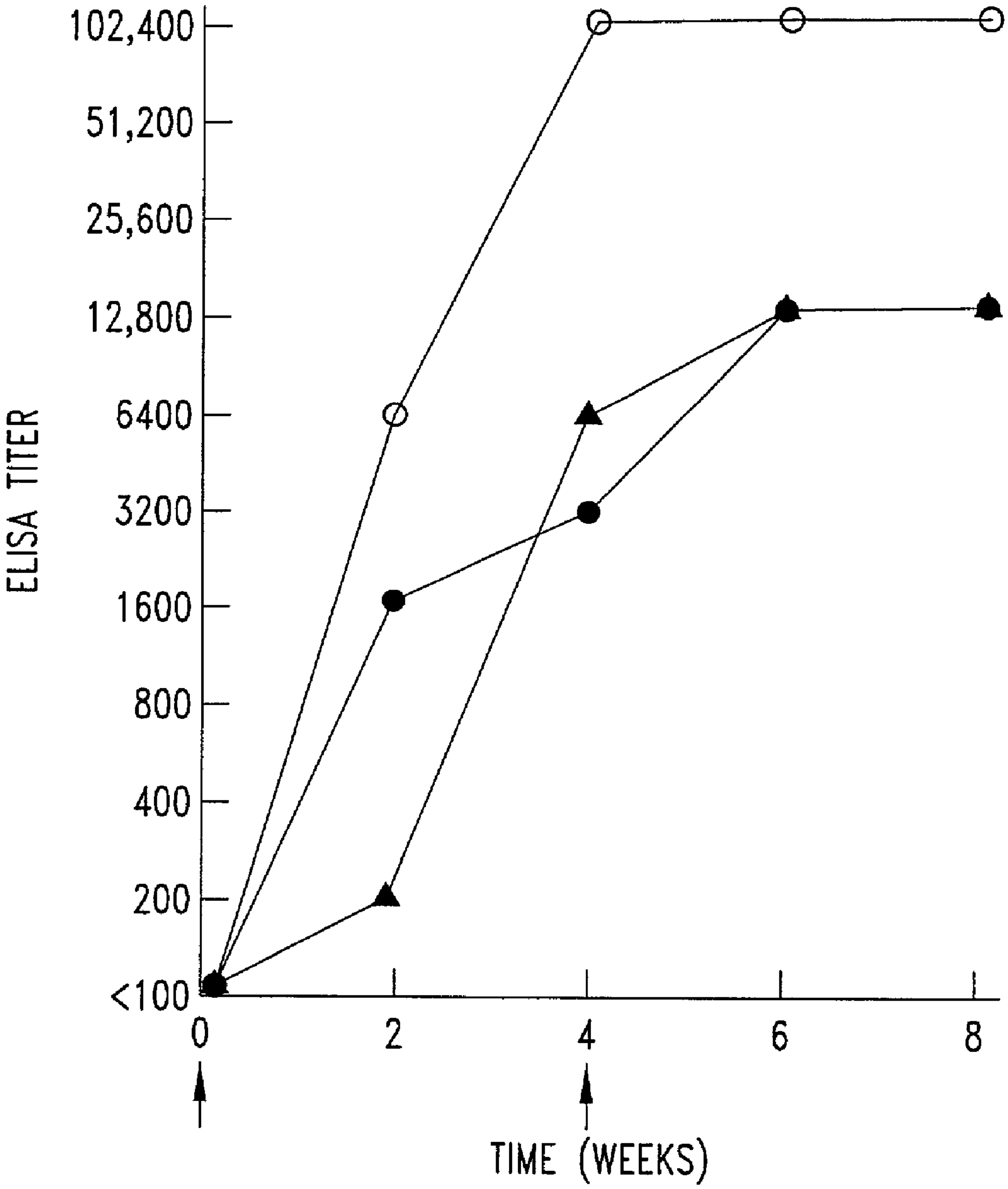
FIG. 3 shows the immunogenicity of LT-B-M24 in rabbits, as determined by ELISA.

FIG. 3 shows immunogenicity of LT-B-M24 in rabbits, as determined by ELISA. Three rabbits (○, ●, Δ) were immunized with 300 μg LT-B-M24 at time 0 and at 4 weeks (arrows) and sera collected at two-week intervals were assayed for the presence of antibodies against pep M24 by ELISA. Titers are expressed as the reciprocal of last dilution of antiserum that resulted in an O.D. of >0.1 at 580 nm. ELISA performed at various intervals after the initial injection of LT-B-M24 revealed a brisk antibody response in all three rabbits, even after a single intracutaneous dose of LT-B-M24.

FIGS. 4A and 4B show a construct of 762 nucleotides (SEQ ID NO:3) coding for an antigen of 254 amino acid residues (SEQ ID NO:4), as shown. The antigen is comprised of an M5 hapten fragment of 16 amino acids. The fragment is joined by a BamH1 restriction site to a carrier, which is the carboxy-terminal half of M5. The carrier includes 2.5 C-repeats, which each commence with the tetrapeptide Asn-Lys-Ile-Ser (SEQ ID NO:19). While there is no amino acid linker linking the fragment and carrier, the BamH1 is a suitable site for insertion of an appropriate linker.

FIGS. 5A and 5B show a construct of 852 nucleotides (SEQ ID NO:5) coding for an antigen of 284 amino acid residues (SEQ ID NO:6), as shown. The antigen is comprised of three segments of M5 designated A, B and C, respectively. The C segment is joined by a BamH1 restriction site to a carrier, which is the carboxy-terminal half of M5. The carrier includes 2.5 C-repeats, which each commence with the tetrapeptide Asn-Lys-Ile-Ser (SEQ ID NO:19). While there is no amino acid linker linking the fragment and carrier, the BamH1 is a suitable site for insertion of an appropriate linker.

DETAILED DESCRIPTION OF THE INVENTION

The above and various other aspects and advantages of the present invention are described hereinafter. All references above and hereinafter are incorporated by reference, and identified in the Bibliography as numbered in the text.

The invention provides for a recombinant hybrid streptococcal M protein antigen which elicits opsonic antibodies to a serotype of Group A *streptoccocus*, which comprises a carrier linked by an amino acid linker to an amino acid fragment, the fragment having at least one epitope of a serotype of Group A streptococcal M protein. The fragment elicits opsonic antibodies to the epitope or epitopes of the target serotype, without eliciting cross-reactive antibodies to mammalian heart tissue antigens.

It is also an embodiment of the present invention that the antigen of carrier and fragment are joined or fused together without the presence of a linker.

The amino acid fragment is of a portion of a streptococcal M protein serotype of Group A *streptoccocus*. The fragment is of a peptide size which is non-immunogenic (or inadequately immunogenic) by itself. In that sense, the fragment may be considered a hapten if it were considered by itself. Where a hapten is defined as a low molecular weight determinant group, which by itself is non-immunogenic, but which becomes so when placed on a larger “carrier” molecule. If coupled to a carrier protein of appropriate size, haptens are capable of inducing a strong immune response in an animal or human.

By the present invention, the recombinant hybrid proteins are selected to be constituted of amino-terminal ($NH_2$) fragments of M proteins which contain immunoprotective epitopes, which elicit opsonic antibodies to a target serotype of Group A streptococcal M protein. The amino terminal fragment of M protein is constituted of the first 35 amino terminal residues of the M protein. These fragments of the present invention do not contain cross-reactive or autoimmune epitopes to generate an autoimmune response directed to heart or other tissue antigens. As a consequence, the risk of developing ARF is minimized. The fragments of the M protein elicit antibodies of the opsonic or serum type which assist the phagocytic engulfment of the Group A *streptoccocus*. The fragments of the M proteins may also elicit, if so desired, protective antibodies, which are secretory or mucosal antibodies, (e.g. from the saliva or nasal membranes), which play a critical role in a first-line defense against an invading *streptoccocus* at the locus or site of infection. In that instance, the fragments are portions of the COOH-terminal half of M proteins, which fragments are free of epitopes which elicit antibodies which cross-react with heart or other tissues.

Thus two types of antibodies are elicited from epitopes located on two different portions of the M protein molecule. The $NH_2$-terminal fragments contain epitopes which elicit serum or opsonic antibodies in immunized mammals. The COOH-terminal fragments of the M protein elicit protective secretory or mucosal immunity in immunized mammals, e.g. IgA antibodies.

It should be noted in conjunction with the invention, as has been described herein, that not all M protein epitopes are sero-specific in their $NH_2$-terminal portion. Some epitopes of particular serotypes, such as M5, do cross-react to some extent with streptococci of a type other than M5, such as M6 or M19. And to some extent, this also occurs with other M serotypes. Accordingly, it is within the scope of the invention that when type-specificity is referred to, this does not exclude some cross-reactivity between certain shared structures of different serotypes. However, one should be careful to note that such shared epitopes that would cross-react with heart tissue are to be excluded from the selected fragments. Also included are $NH_2$-terminal fragments which, in addition to evoking opsonic antibodies, also contain epitopes that evoke protective secretory or mucosal antibodies.

A mixture or cocktail of antigens is provided. The antigens in the mixture contain $NH_2$ or COOH-terminal fragments of M protein of different serotypes which can elicit opsonic and protective antibodies, respectively, to a wide range of serotypes, particularly the rheumatogenic streptococci.

Thus, if it is desired in accordance with the invention to provide immunity against *streptoccocus* infections that are likely to cause rheumatic fever, DNA molecules will be constructed which code for $NH_2$-or COOH-terminal fragments which contain epitopes that elicit opsonic or protective to antibodies types 1, 3, 5, 6, 14, 18, 19, 24, 27 or 29 M proteins, for instance and linked in tandem by an amino acid linker or fused directly with an appropriate carrier.

Suitable portions of $NH_2$-terminal fragments are from 10 to 35 amino acid residues in length. Fragments of this length have been shown to elicit opsonic antibodies but not to contain heart-cross reactive epitopes. Any portion of the amino terminal fragment is suitable as long as the fragment, when constituting a portion of the antigen of the invention, will elicit opsonic antibodies. An example of a suitable amino terminal portion is that portion containing amino acid residues 14 to 26 of the amino terminal fragment of the M protein.

Examples of suitable $NH_2$-terminal fragments of M protein for constructing antigens, which elicit opsonic antibodies in an immunized animal are described hereinafter. For M24, there is provided a 15 amino acid fragment of the order Val-Ala-Thr-Arg-Ser-Gln-Thr-Asp-Thr-Leu-Glu-Lys-Val-Gln-Glu (SEQ ID NO:7). For M5, there is provided a 15 amino acid fragment of the order Ala-Val-Thr-Arg-Gly-Thr- Ile-Asn-Asp-Pro-Gln-Arg-Ala-Lys-Glu (SEQ ID NO:8). For M6, there is provided a 15 amino acid fragment of the order Arg-Val-Phe-Pro-Arg-Gly-Thr-Val-Glu-Asn-Pro-Asp-Lys-Ala-Arg (SEQ ID NO:9). For M19, there is provided a 15 amino acid fragment of the order Arg-Val-Arg-Tyr-Thr-Arg-His-Thr-Pro-Glu-Asp-Lys-Leu-Lys-Lys (SEQ ID NO:10). For M3, there is provided a 15 amino acid fragment of the order Asp-Ala-Arg-Ser-Val-Asn-Gly-Glu-Phe-Pro-Arg-His-Val-Lys-Leu (SEQ ID NO:11). For M1, there is provided a 15 amino acid fragment of the order Asn-Gly-Asp-Gly-Asn-Pro-Arg-Glu-Val-Ile-Glu-Asp-Leu-Ala-Ala (SEQ ID NO:12). For M18, there is provided a 15 amino acid fragment in the order Ala-Pro-Leu-Thr-Arg-Ala-Thr-Ala-Asp-Asn-Lys-Asp-Glu-Leu-Ile (SEQ ID NO:13). For M12, there is provided a 15 amino acid fragment of the order His-Ser-Asp-Leu-Val-Ala-Glu-Lys-Glu-Arg-Leu-Glu-Asp-Leu-Gly (SEQ ID NO:14). These $NH_2$-terminal fragments will elicit opsonic antibodies in immunized animals when linked or fused to an appropriate carrier, which carrier may also favorably elicit desirable antibodies. These, as well as other antigens of the present invention may be administered to a mammal as a cocktail or mixture to elicit broad-spectrum antibodies. In such fashion, broad spectrum immunity is provided to immunized mammals against Group A streptococci.

It is important to note that the invention is not limited to a particular amino acid sequence, wherever amino acid sequences are referred to or described, as above. In any particular amino acid sequence or fragment referred to herein, any one or more amino acids can be removed, substituted or replaced by some other amino acid(s), providing that the desired epitopes are not adversely affected by such changes in the primary structure of the protein fragments. Indeed, this is a quite common occurrence for the M protein among various strains within the same serotype. This tendency of variation in the sequence of the M protein has been shown for several such M proteins.

Accordingly, any single fragment of a given serotype encoded by a gene may have its sequence altered, so as to carry multiple epitopes for a multitude of strains within the same serotype. In this fashion, a single antigen will elicit desirable antibodies to a number of strains within the same serotype. It is therefore an important concept of the invention that once reference is made to a particular serotype (i.e., of any one of the known or to be discovered serotypes, e.g., 1–82), reference is not intended to one single strain of a type, but to the various strains within the serotype. Thus, not only is it a fundamental concept of the invention to provide a vaccine of a cocktail or mixture against different serotypes, but also a vaccine directed to different strains within that particular serotype.

Thus, in accordance with the invention, there is provided a vaccine which is effective against not only different serotypes of M proteins, but also against various strains within the individual serotypes.

The amino acid linker sequences ideally contribute to the maximum accessibility of the epitopes of the fragments so as to generate the desired antibodies. Thus the linkers may function to influence the orientation, conformation or other aspects of the amino acid fragment -carrier molecule. Ideally, the linkers contribute to the orientation so that the hybrid molecule, or at least the amino acid fragment, mimics the native molecule.

The linker amino acid sequence is provided by construction of a gene coding for the desired M protein amino acid sequence and carrier with a restriction site to permit insertion of the DNA coding for the linker between the sequences of the fragment and the carrier, which linker links the carrier and fragment in tandem. Illustratively, such a linker is a proline-rich linker of Pro-Gly-Asn-Pro-Ala-Val-Pro (SEQ ID NO:15). Other amino acid linkers may be used such as Ile-Pro-Gly, Asp-Pro-Arg-Val-Pro-Ser-Ser (SEQ ID NO:16) or His-Gly. An amino acid linker of Asp-Pro-Arg-Val-Pro-Ser-Ser (SEQ ID NO:16) or its equivalent is also considered suitable (SEQ ID NO:18). While in theory, a linker could be constituted by one amino acid, so long as the desired immunoreactive conformation is achieved, longer linker regions may be more suitable to optimize the immunogenicity of the epitopes.

The effect of the different linkers on the immunogenicity of the hybrid molecule may justify further investigations. It is not excluded that, depending on the type and number of the amino acids of the linker, a hybrid antigen of ideal or close to ideal high immunogenicity may be identified.

A linker of hydrophobic acids is most desirable, such as tryptophan, alanine, leucine, isoleucine, valine, tyrosine, phenylalanine, proline, methionine and combinations thereof. The linkers may range in number from 2 to 30, providing that there is no adverse effect on the immunogenicity of the molecule. Quite satisfactory results have been obtained with a two amino acid linker of His-Gly, suggesting that such a small molecule may be satisfactory for M protein components. The sequence of the amino acids in any particular linker does not appear at this time to be critical.

As described further below, linkers are useful but not essential to join the carrier and fragment. The carrier and fragment may be joined or fused together directly.

According to the present invention, gene constructs are provided which encode an amino-terminal fragment of an M protein serotype linked with the carboxy-terminal half of an M protein, which functions as a carrier. See FIGS. 4A–B and 5A–B (SEQ ID NOS: 3,4,5, and 6, respectively). As shown therein, a BamH1 restriction site serves as a junction between the fragment and carrier. It is contemplated and within the scope of the invention that the restriction site be a suitable site for insertion of an appropriate amino acid linker. The carboxy-terminal carrier may elicit protective mucosal or secretory antibodies to serotypes of M protein. These antibodies may play an important role in preventing colonization and infection by Group A streptococci. Such a carrier thus serves a dual purpose. It serves the function of introducing the epitope(s) present on the amino-terminal hapten fragment to the macrophages for processing and antigen presentation to helper T cells for generating a type-specific humoral response. And the carrier possesses epitopes which may elicit more broadly protective IgA antibodies at the mucosal or secretory level. These antibodies are more broadly protective than the type-specific opsonic type, as they share more homologous epitopes among the various types of rheumatogenic streptococci. In this fashion, such protective antibodies are advantageously of a cross-protective or cross-serotype nature.

Instead of using the entire carboxyl-terminal of any one of the serotypes, it may be advantageous and desirable to only use one or more C-repeats of the M protein as a carrier. It is noteworthy that the carboxyl-terminal portion of M protein used in the construct need not be one of the same serotype as that which constitutes the amino terminal portion of the construct.

Instead of using the COOH-terminal portion or half of an M protein as a carrier, other suitable carriers for the fragments include surface proteins from gram-positive cocci (mostly from streptococci and staphylococci) (32). These proteins, which have been sequenced, are IgA binding protein (ARP 4), $F_c$ binding protein ($F_cRA$), human IgG $F_c$ binding protein (Protein H), C5a peptidase (SCP) and T6 surface protein from *S. pyogenes;* wall-associated protein (wap A) and cell surface protein (PAc and spa P) from *S. mutans:* Protein G, an IgG binding protein from Group G streptococci, Protein A and fibronectin binding protein (FaBP) from *S. aureus,* and a cell wall protease (wg 2) from *S. cremoris*. Beginning at the C-terminal end of these molecules, these proteins and the M proteins all have a similar arrangement of amino acids. Up to seven charged amino acids are found at the C-terminus which are composed of a mixture of both negative and positive charged residues. Immediately, N-terminal to this short charged region is a segment of 15–22 predominately hydrophobic amino acids. Beginning about nine amino acids N-terminal from the hydrophobic domain is found a hexapeptide with the consensus sequence LPSTGE (SEQ ID NO:17), that is extremely conserved among all the proteins. Analysis of 12 of these surface molecules revealed that these proteins contain repeat segments, as in the M proteins, and were predominately helical within the region containing the repeat segments.

These proteins, as carriers, can be linked in tandem by an amino acid linker to $NH_2$ or COOH-terminal fragments or fused directly with the fragments, so long as the immunogenicity of the antigens is not adversely affected.

The amino acid fragments of the present invention are linked, either with or without a linker, to an appropriate carrier. For this purpose, any type of carrier is contemplated so long as the amino acid fragment linked to the carrier generates an opsonic or protective immune response to the epitopes of the fragment. The carrier may be a molecule which is free of an epitope which elicits antibodies to a serotype of streptococcal M protein. An example would be the B subunit *E. coli* labile toxin (LT-B). Alternatively, the carrier may be selected from the COOH-terminal portion of the M protein which is not cross-reactive with human tissue, and which may favorably elicit protective mucosal antibodies. Or the carrier may be the COOH-terminal portion of surface proteins of gram-positive cocci, as described above.

Other examples of suitable carriers may be keyhole limpet hemocyanin (KLH), tetanus toxoid, diphtheria toxoid, bovine serum albumin, hen egg lysozyme, gelatin, bovine gammaglobulin and flagellin polymer.

As shown in FIGS. 4A–B (SEQ ID NOS: 3 and 4, respectively) and 5A–B (SEQ ID NOS: 5 and 6, respectively), it is an embodiment of the present invention that the presence of one or more linker in the gene constructs, linking in tandem the fragment and carrier, is not required to elicit opsonic or protective antibodies in an immunized host. The fragment and carrier, in this embodiment of the invention, are fused directly to each other. A fusion antigen is suitable so long as the immunogenicity of the antigen is not adversely affected. The resulting gene constructs are fusion constructs.

Alternatively, a linker of amino acids may be added by chemical means after the antigen is expressed, e.g., by treatment with succinimidyl-4-(N-maleiamido-methyl) cyclohexone-1-carboxylate.

It is also contemplated that the constructs of the invention be constructed to contain a fragment of the $NH_2$ or COOH-terminal region of serotypes, which are not known to have a rheumatogenic effect, as those types described above and in the literature. In those instances, where such fragments have not yet been sequenced or not yet been published, whether rheumatogenic or non-rheumatogenic, one skilled in the art can sequence such structures by methods readily available. The invention also includes the construction of hybrid constructs containing repeating amino-terminal or carboxyl-terminal M protein fragments using PCR. One skilled is the art can utilize homologous regions of published M protein emm gene sequences from Group A streptococci (GAS; *Streptococcus pyogenes*) to design three primer pairs for PCR and three oligonucleotide probe sequences internal to the amplified products. One set of primers and corresponding probe can detect and lead to amplification of emm (–like) genes of virtually every type ("all M"). Another set ("SOR$^-$M") amplifies only emm (–like) genes from GAS negative for serum opacity reaction (SOR). And a third set ("SOR$^-$M") expands only emm (–like) genes from SOR$^-$ GAS. Using the "all M" primer pair for PCR on the genomic DNA from gas of 29 different M types, as well as from a Group C and a Group G streptococcal isolate, DNA fragments within the expected size range were amplified in every assay. All PCR products reacted with the "all M" probe.

Thus, the invention contemplates a hybrid fragment-carrier protein antigen encoded by an appropriate gene or genes to express in an appropriate organism, the antigen that will elicit the desired antibodies. Thus encompassed within the scope of the present invention are antigens comprised of opsonic antibody-generating $NH_2$ or COOH-terminal fragments of M protein from all the known rheumatogenic types of streptococci, and fragments from types of streptococci which are not, or at least not yet known or shown to be, associated with ARF. An example of a non-rheumatogenic streptococcal type, the M protein antigen of which is within the scope of the invention, is type 12.

The appropriate genes of the present invention are constructed and expressed, as described hereinafter. The genes encoding the appropriate carriers of the present invention are inserted into appropriate plasmids. Non-limiting examples of the appropriate carriers are the carboxyl-terminal half of M proteins, the carboxyl-terminal half of surface proteins of gram-positive cocci and the B subunits of *E. coli* labile (LT-B) and cholera toxin (CT-B) from *Vibrio cholerae.* The plasmids are modified to contain a small polylinker with three endonuclease restriction sites at the 3' end, followed by transcription terminators in each reading frame. The selected genes encoding the desired $NH_2$ or COOH-terminal fragments of M protein are constructed in a suitable manner. For instance, a pair of oligonucleotides coding for the fragments are synthesized using an automated DNA synthesizer (ABI, mode 1381A). The desired oligonucleotides copy the appropriate first number of base pairs of the genes encoding the desired $NH_2$ or COOH-terminal fragments of M protein. Additionally, the oligonucleotides encompass the right hand side of an appropriate restriction site at the 5' end, for instance NcoI. The oligonucleotides are mixed in equimolar ratios, heated to an appropriate temperature and allowed to anneal at ambient temperature. The appropriate plasmids are digested with restriction enzymes, and the cut plasmids are then purified. For instance, plasmid pPx1604 was digested with NcoI and EcoRV and purified from agarose gels over glassmilk (Geneclean, Bio 101, La Jolla, Calif.). The synthetic oligonucleotide pairs of interest are then ligated into the cut sites of the plasmids. The plasmids containing the M protein fragments of interest are then used to transform an appropriate microorganism. For instance, *E. coli* JM105 is a suitable microorganism. Transformants are then screened by an appropriate method, e.g., dot blot analysis using appropriate antisera.

For high level expression of the M protein antigens of the present invention, insertion of the selected gene constructs, encoding the antigens, into suitable plasmids is carried out. An example of a suitable plasmid is pK K223-3 (Pharmacia, Uppsala, Sweden). The genes are cut from suitable plasmids, for instance pPX1604, with appropriate restriction enzymes. Suitable enzymes are EcoRI and SalI. The selected genes are purified by cutting from agarose gels. Klenow fragment is used to end repair the purified DNA. The purified gene constructs are cut with suitable restriction enzymes, for instance EcoRI. The cut gene constructs are then ligated into the appropriate restriction sites of selected high expression plasmids. For instance, the cut genes are ligated into the EcoRI and SmaI restriction enzyme sites of pKK223-3 plasmids. The selected plasmids carrying the gene constructs of the present invention are then used to transform suitable microorganisms. For example, *E. coli* JM105 is transformed with the selected plasmids. Expression of the proteins is detected in a suitable fashion, such as by dot blot analysis using appropriate antisera. For example, the desired transformants were screened for expression of the gene encoding a $NH_2$-terminal fragment' of M24-LT-B carrier (subunit B of *E. coli* labile toxin) by dot blot analysis using rabbit antisera against a synthetic peptide of M24, SM24 (1–29) C and rabbit antiserum against purified LT-B (16), kindly provided by Dr. John Clements of Tulane University. The appropriate positive transformants harboring the selected plasmids carrying the genes of the present invention are selected for expression and purification of the recombinant protein antigens of the present invention.

The vaccine compositions of the invention include the antigens of the invention and biologically acceptable diluents or adjuvants. The compositions are suitable for eliciting opsonic and/or protective antibodies to serotypes of M protein of Group A *streptoccocus*. The administered compositions of the present invention elicit antibodies, without eliciting cross-reactive antibodies to mammalian heart tissue antigens.

Appropriate biologically acceptable diluents or adjuvants for the present composition may be selected from a wide group of such diluents or adjuvants as readily known to one of skill in the art. A non-limiting example of a diluent is phosphate-buffered saline. The compositions may be administered singly or as a mixture or cocktail.

Another aspect of the present invention are hybrid or fusion genes which have been constructed which encode the antigens of the present invention. The fusion genes code for the antigens of the invention, constituted as described above, of amino acid fragments linked to the selected carrier. The genes are inserted into suitable self-replicating vehicles, like plasmids. The plasmids containing the genes are then used to transform nonvirulent microorganisms. The transformed microorganisms express the hybrid or fusion protein antigens which are capable of eliciting opsonic and/or protective antibodies against serotypes of Group A *streptoccocus* in immunized mammals, without eliciting cross-reactive antibodies to mammalian heart tissue antigens.

One method provides for administration of the compositions to mammals, in particular humans, to elicit opsonic and/or protective antibodies directed to epitopes present in the hybrid antigens of the present invention. No antibodies cross-reactive with heart tissue antigens are elicited. The method comprises administering orally to said mammal, in an amount effective to confer immunity against Group A streptococci infection, a therapeutic composition which comprises a biologically acceptable carrier and a non-virulent, live bacterium as described in U.S. Pat. No. 5,124,153 to Beachey et al., and all references therein incorporated herein by reference. The bacterium is transformed with a plasmid encoding and expressing an antigen of the present invention. The antigen is released from the bacterium, whereby protective antibodies to the antigen of the same serotype as the immunizing antigen are elicited, without eliciting antibodies which are cross-reactive with heart tissue antigens. Immunity against streptococci infection is thereby conferred to the mammal.

The present invention encompasses administering orally multiple therapeutic compositions. Each composition comprises a hybrid antigen of a serotype of *streptococcus*. The compositions may be administered individually or as a mixture or cocktail of several compositions. In this fashion, a mammal is immunized against one or more rheumatogenic serotypes of Group A *streptococcus*. Broad spectrum protective immunity may therefore be established against all rheumatogenic streptococci.

Any biologically acceptable carrier may be used. A biologically acceptable carrier may be PBS, as a non-limiting example. Particularly preferred is a dose of the therapeutic composition suspended in 25 ml of PBS, pH 7.2 containing 5 mg/ml kanamycin sulfate and 1 mg/ml each of paraaminobenzoic acid (PABA) and 2,3-dihydrobenzoic acid (DHB).

In accordance with the invention, it is preferable that the plasmids which encode the M protein genes of the present invention be cloned first and expressed in *Escherichia coli.* Any other enteric *bacilli* of the coliform group such as *Klebsiella* or *Enterobacter* can be used, but normally *E. coli* is preferred. Therefore the plasmid carrying the M gene is isolated and purified and then a construct is built to transform the desired non-virulent bacteria, such as the araA–*S. typhimurium* (SL3261). It is to be noted that this mutant strain exhibits a nutritional marker both for PABA and 2,3-DHB. It is to be noted that another desired specie of *S. typhimurium* is recA–*S. typhimurium,* particularly strain Ty21a (17).

It may be desired to obtain the M protein gene from a virulent strain of *S. pyogenes*. However, it is preferable to obtain the gene from an attenuated, non-virulent strain of *S. pyogenes*, or to fabricate the nucleotide sequence coding for the desired M protein.

The recombinant DNA cloning vectors of the present invention are not limited for use in a single species or strain of *Salmonella*. To the contrary, the vectors are broadly applicable and can be transformed in host cells of other gram negative bacteria such as of the *Enterobacteriaceae* genus (such as *Shigella* and *Klebsiella* like (*Klebsiella pneumoniae; Enterobacter* like *Enterobacter aerogenes. Salmonellae*, such as *Salmonella arizona,* and Citrobacter may be used if appropriately rendered non-virulent or attenuated.

Common *Salmonella* species which may be used when attenuated and rendered non-virulent include the following: *S. paratyphi A, S. schottmulleri, S. typhimurium, S. paratyphi C, S. choleraesuis, S. Montevideo, S. newport, S. typhi, S. enteritidis, S. gallinarum,* and *S. anatum.*

In accordance with the invention there may also be used as host for the recombinant DNA cloning vectors of the present invention bacteria of the *Streptococcus* genus which are non-virulent or which have been made non-virulent or attenuated, including streptococci of the immunological groups A–O but generally other than A. Suitable Streptococci which can be used as bacterial host include *S. cremoris, S. faecalis, S. salivarius, S. mitior, S. mitis, S. mutans* and *S. sanguis*. Particularly preferred is *S. mutans* which is non-cariogenic.

Additional appropriate microorganisms which may be attenuated and transformed in accordance with the invention are known.

Generally any enteric bacterium may serve as the host bacterium. It is preferable that the host bacterium only survive in the subject long enough to elicit the opsonic response, but generally any bacterial strain that has been attenuated so as not to colonize yet still multiply to a limited degree to elicit antibodies to the protein antigen of the present invention can be used. In a preferred embodiment of the invention the $Aro^-$ strain of *S. typhimurium* is used, which requires two metabolites not found in mammalian tissues, PABA and 2,3-DHB. As a result, the inoculated bacteria die after several generations from a lack of these metabolites.

However, any mutated microbial agent with a metabolic deficiency for nutritional compounds not found in the tissues of the subject to be immunized, or one so made by genetic manipulations, may be employed.

It is to be noted that the non-virulent $aro^-$ *Salmonella typhimurium* SL3261 which has been transformed with a plasmid containing a recombinant hybrid gene encoding a protein antigen expressed the M5 protein molecule, which expression is confined almost exclusively to the *S. typhimurium* cytoplasmic compartment. It is unique and unexpected aspect of this invention that an immunogenic and protective surface antigen such as the Streptococcal M protein antigen is expressed in the cytoplasm of the non-virulent host bacterium.

Thus it can be seen that in accordance with the invention, the desired nucleotide sequence which codes for and expresses the protein antigen, which is effective to elicit opsonic and/or protective antibodies to streptococcal serotypes, can be cloned into a variety of hosts. In a broader sense therefore, the transformed host in which the nucleotide sequence is found after replication need not be heterologous with respect to the nucleotide sequence, nor does the sequence need to be heterologous with respect to the microorganisms.

In accordance with a specific embodiment of the method of immunization of a warm-blooded animal, it has been shown that a) peroral administration of up to $1.65\times10^9$ mutant non-virulent *Salmonella* containing the plasmid pMK207 encoding an antigen of serotype M5 was well tolerated in mice; b) plasmid mPK207 was extremely stable both in vitro and in vivo; c) the mice receiving the highest dose ($10^9$) of bacteria harbored the microorganisms in the liver for as long as three weeks without ill effects; d) the mice immunized orally with non-virulent transformed *Salmonella* expressing the gene developed opsonic serum antibodies as early as three weeks against serotype M5 Streptococci; and e) the immunized mice were completely protected at three weeks against intro-peritoneal challenges of the homologous serotype M5 (but not the heterologous serotype M24) Streptococci.

It is noteworthy that no cross-reactive immunity is observed when the composition of the invention is administered orally. The cytoplasmic expression of the M protein antigen in the non-virulent bacterium is especially advantageous for this oral administration. The antigen is protected within the cytoplasm of the non-virulent bacterium from the acids of the stomach and other damaging agents until the non-virulent cell dies and releases the antigen, ordinarily in the small intestine, which is the preferred location for delivery of the antigens.

In accordance with the invention the non-virulent bacterium may also be used as a host for recombinant DNA cloning vectors containing nucleotide sequences which code for and express the immunogenic protein antigens of the present invention which are specifically effective to confer immunity against Streptococcal infections and which are not cross-reactive with human tissue antigens, especially those of the heart.

The therapeutic compositions of the present invention may also be administered parenterally. Mammals, in particular humans, immunized parenterally with a sufficient amount of the therapeutic composition of the present invention develop opsonic and/or protective antibodies directed to the epitopes of the hybrid streptococcal M protein antigen. Non-limiting examples of such parenteral routes of administration are intracutaneous and intramuscular.

For intracutaneous injection, 100–300 μg of hybrid antigen emulsified in complete or incomplete Freund's adjuvant was administered in a mammal. A booster injection of about the same dose in saline was administered about one month later. Blood was obtained prior to the first injection and at two-week intervals thereafter for eight weeks.

A topical method of administration is also provided, namely intranasal.

For intranasal administration, a mammal received about 50 μg to about 10 mg of purified antigen in an appropriate diluent for administration.

In accordance with the invention, the therapeutic composition may be administered singly in series or advantageously in a mixture or cocktail of multiple compositions to elicit broad spectrum immunity versus Group A streptococci.

Other advantages of the invention will appear from the non-limiting materials, methods and examples which follow.

EXAMPLE I

Purification of LT-B-M24 hybrid protein. The recombinant LT-B-M24 protein was purified from cell extracts of JM105 (harboring pEC.LT-B-M24) grown overnight in one liter of L-broth supplemented with 75 μg/ml ampicillin, 25 μg/ml streptomycin and 1 mM isopropylthiogalactoside (IPTG, Bethesda Research Laboratories, Inc., Bethesda, Md.). -The cells were pelleted at 7,000×g and resuspended in 50 ml 100 mM carbonate buffer, pH 11, containing 100 μg/ml lysozyme, 1 mM ethylenediaminetetraacetic acid (EDTA, Sigma Chemical Co., St. Louis, Mo.) and 100 μg/ml phenylmethylsulfonylfluoride (PMSF, Sigma Chemical Co.) and incubated at 37° C. for 30 minutes. The cells were centrifuged at 7,000×g and the supernatant was dialyzed against distilled water and lyophilized. Purification was performed by loading 50 mg of hybrid protein extract onto a preparative polyacrylamide gel electrophoresis unit (Prep Cell, Model 491, Bio Rad., Inc.) using a 37 mm column and a 9 cm 11% polyacrylamide gel. Six ml fractions were collected and assayed for the presence of recombinant protein by Western blot analysis using rabbit antiserum against pep M24. Fractions containing activity were pooled, dialyzed and lyophilized.

EXAMPLE 2

Immunization of rabbits. Rabbits were immunized intracutaneously with 300 μg LT-B-M24 protein emulsified in complete Freund's adjuvant. A booster injection of the same dose in saline was given four weeks later. Blood was obtained prior to the first injection and at two-week intervals thereafter for eight weeks.

EXAMPLE 3

Assay for M protein antibodies. Rabbit antisera were assayed for the presence of M protein antibodies by ELISA using LT-B, pep M24 or SM24 (1-29)C as solid phase antigens, as previously described. Opsonic antibodies against type 24 streptococci were assayed by in vitro opsonophagocytosis tests. Briefly, 0.1 ml of test serum was added to 50 μl of a standard suspension of streptococci. 0.4 ml heparinized, non-immune normal human blood was added and the mixture was rotated end-over-end for 30 minutes. The presence of opsonic antibodies was estimated by counting the percentage of neutrophils with associated streptococci (percent opsonization) on stained smears. Indirect bactericidal assays were performed using the same mixture as described above except that fewer streptococci were added. The tubes were rotated for three hours and pour plates were made using 0.1 ml of the test mixture in 5% sheep blood agar. CFU of streptococci surviving were counted after incubating overnight at 37° C.

EXAMPLE 4

Assay for heart-crossreactive antibodies. Rabbit antisera against LT-B-M24 were screened for the presence of heart-crossreactive antibodies by indirect immunofluorescence assays using thin sections (4 μ) of human myocardium, as previously described.

EXAMPLE 5

Mouse protection tests. Passive mouse protection tests were performed as previously described. Briefly, Balb/c mice were injected intraperitoneally with 0.5 ml test serum, and 24 hrs later, groups of mice were challenged intraperitoneally with 10-fold dilutions of type 24 streptococci. Pour plates were performed to determine the CFU of streptococci that each group received. The $LD_{50}$ was calculated using the method of Reed and Muench.

EXAMPLE 6

Assay for M protein epitopes that evoke mucosal antibodies broadly protective against infection. Rabbit antisera were screened for the presence of broadly protective antibodies using passive mouse protection assays. Antisera were first tested for their ability to react with the surface M protein of multiple heterologous serotypes of Group A streptococci by ELISA. Those that recognized M protein epitopes in their native conformations were then used to passively protect mice against intranasal challenge infections. Antibodies were absorbed to virulent streptococci and mire were challenged intranasally with $10^7$ CFU. Throat cultures were obtained on alternate days and deaths were counted over the ensuing 14 days.

By way of the Examples, it is shown that the antigens of the present invention elicit opsonic and/or protective antibodies directed to epitopes on the antigens, and confer immunity to immunized mammals against Group A streptococci. The antigens may be advantageously mixed to form a cocktail.

Materials and Methods

Construction and expression of LT-B-M24 fusion gene. Plasmid pPX1604, which contains the gene for LT-B, was kindly provided by Robert Brey, Praxis Biologics, Rochester, N.Y. pPX1604 is a derivative of pJC217 and was modified to contain a small polylinker with three endonuclease restriction sites at the 3' end followed by transcription terminators in each reading frame. The M24 component of the hybrid gene consisted of a pair of oligonucleotides that were synthesized using an automated DNA synthesizer (ABI, model 381A). The oligonucleotides copied the first 36 base pairs of the emm24 gene and included the right hand side of an NcoI site on the 5' end. The oligonucleotides were mixed in equimolar ratios in ligation buffer, heated to 65° and allowed to anneal at ambient temperature. Plasmid pPX1604 was digested with NcoI and EcoRV and the cut plasmid was purified from agarose gels over glassmilk (Geneclean, Bio101, La Jolla, Calif.). The synthetic M24 oligonucleotide pair was then ligated into the NcoI and EcoRV sites of pPX1604. The ligation mixture was used to transform *E. coli* strain JM105. Transformants were screened for expression of M24 and LT-B by dot blot analysis using rabbit antisera against a synthetic peptide of M24, SM24 (1-29)C, and rabbit antiserum against purified LT-B. The purified LT-B was kindly provided by Dr. John Clements, Tulane University.

For high level expression of the fusion protein, the LT-B-M24 gene was inserted into pK K223-3 (Pharmacia, Uppsala, Sweden). The hybrid gene was cut from pPX1604 with EcoRI and SafI and the fragment was purified by cutting from agarose gels. Klenow fragment was used to end repair the purified DNA which was then cut with EcoRI and ligated into the EcoRI and SmaI restriction enzyme sites of pK K223-3. The ligation mixture was used to transform JM105 and expression of the LT-B-M24 hybrid protein was detected by colony blots as described above. One positive transformant harboring pKK223-3 that contained the hybrid LT-B-M24 gene (pEC.LT-B-M24) was selected for expression and purification of the recombinant protein.

DNA sequencing.

The LT-B-M24 gene (SEQ ID NO:1) was sequenced using double-stranded plasmid DNA and $^{32}P$-labeled dNTPs by the dideoxy chain-termination method of Sanger. Synthetic oligonucleotides copying the sense strand of pK K223-3 at the EcoR1 site, bases 289–303 of the LT-B gene, and the antisense strands of the HindIII site of pK K223-3 provided sequence data that confirmed the location of the start codon of the LT-B component of the gene, the position of the M24 synthetic oligonucleotide pairs and the NcoI site.

Results

Immunogenicity of LT-B-M24 hybrid protein. Rabbits immunized with LT-B-M24 developed high titers of antibodies against LT-B, pep M24 and SM24 (1-12)C, as determined by ELISA (Table 1). Interestingly, the antibody titers against the synthetic peptide were equivalent to those against the native pep M24, suggesting that the majority of the M24 antibodies evoked by the LT-B-M24 hybrid recognized M protein epitopes in the native molecule. Immune sera from all three rabbits opsonized type 24 streptococci, indicating that the M protein antibodies were directed against protective epitopes of the surface M protein (Table 1). None of the antisera cross-reacted with human myocardial tissue (data not shown). ELISAs performed at various intervals after the initial injection of LT-B-M24 revealed a brisk antibody response in all three rabbits, even after a single intracutaneous does of LT-B-M24 (FIG. 3).

The rabbit antisera raised against LT-B-M24 contained type-specific, bactericidal antibodies against type 24 streptococci (Table 2). All three antisera had significant bactericidal activity against type 24 streptococci, which in some instances was equivalent to that observed with antiserum against intact pep M24. None of the antisera had bactericidal activity against type 5 streptococci, indicating the type-specificity of the M24 epitopes included in the LT-B-M24 hybrid protein. Passive mouse protection tests performed with antisera from rabbit #9146 indicated that antibodies against LT-B-M24 provided significant protection from death compared to pre-immune serum after intraperitoneal challenge with type 24 streptococci (Table 3). In a separate experiment, the $LD_{50}$ of type 24 streptococci in this assay was $1.5\times10^5$ CFU after intraperitoneal injections of preimmune serum, whereas the $LD_{50}$ after giving LT-B-M24 antiserum was $2.5\times10^6$.

TABLE 1

Immunogenicity in rabbits of LT-B-M24 hybrid protein

| Rabbit Number | ELISA titer against: LT-B | pep M24 | SM24 (1-12) C | % Opsonization of Type 24 *Streptococci* |
|---|---|---|---|---|
| 9146 preimmune | <100 | <100 | <100 | 0 |
| 8 wk | 12,800 | 102,400 | 102,400 | 98 |
| 9147 preimmune | <100 | <100 | <100 | 0 |
| 8 wk | 12,800 | 12,800 | 12,800 | 98 |
| 9148 preimmune | <100 | <100 | <100 | 0 |
| 8 wk | 12,800 | 12,800 | 25,600 | 98 |

TABLE 2

Type-specific, bactericidal antibodies evoked in rabbits by LT-B-M24 hybrid protein

| Rabbit Serum* | Number of CFU surviving a 3 hr rotation in test mixture: Type 24 *streptococci* Inoculum: 8 | Type 24 *streptococci* 2 | Type 5 *streptococci* 4 | Type 5 *streptococci* 1 |
|---|---|---|---|---|
| Preimmune Pool | TNTC¶ | 1910 | TNTC | 2060 |
| 9146 | 5 | 5 | TNTC | 1660 |
| 9147 | 15 | 0 | TNTC | 1915 |
| 9148 | 40 | 0 | TNTC | 1830 |
| Anti-pep M24 | 0 | 0 | TNTC | N.D. |
| Anti-pep M5 | N.D. | N.D. | 10 | 0 |

*Preimmune sera were pooled equally for the control. Immune sera were obtained 6 wks after the initial injection of LT-B-M24.
¶*TNTC, too numerous to count, which generally indicates >2,000 CFU.

TABLE 3

Passive protection of mice challenged intraperitoneally with type 24 *streptococci* by antiserum against LT-B-M24 hybrid protein

| Antiserum* | # Dead/# Challenged with: 13,000 CFU | 100,000 CFU |
|---|---|---|
| Preimmune | 5/5 | 8/8 |
| Anti-LT-B-M24 | 1/5 (p < .03)¶ | 1/8 (p < .001) |

*Mice were given 0.5 ml serum i.p. and 24 hrs later were challenged i.p. with virulent *streptococci*. Deaths were recorded for one week.
¶Statistical analyses were performed using the Fisher exact test on Multi-Stat Software (Biosoft, Cambridge, UK).

It is to be understood that the examples and embodiments described above are not limiting and are for illustrative purposes only and that various modifications or changes in light thereof will be suggested to persons skilled in the art and are to be included within the spirit and purview of this application and the scope of he appended claims.

I claim:

1. A cocktail composition, comprising a mixture of at least two different recombinant hybrid Group A streptococcal M protein antigens, wherein said each recombinant hybrid Group A streptococcal M protein antigen comprises a carrier protein fused to at least one amino-terminal peptide fragment of a Group A streptococcal M protein, said peptide fragment having an epitope that elicits opsonic antibodies to at least one Group A atreptococcal serotype and that does not elicit antibodies that cross-react with mammalian tissue antigens.

2. The cocktail composition of claim 1 wherein the amino-terminal peptide fragment of the Group A streptococcal M protein contains 10 amino acids to 35 amino acids.

3. The cocktail composition of claim 1 wherein the amino-terminal peptide fragment of the Group A streptococcal M protein contains 15 amino acids.

4. The cocktail composition of claim 1 wherein the carrier protein elicits mucosal antibodies.

5. The cocktail composition of claim 1 wherein the carrier protein is free of an epitope that elicits antibodies to a serotype of streptococcal M protein.

6. The cocktail composition of claim 1 or 5 wherein said each recombinant hybrid Group A streptococcal M protein antigen comprisies the same or different carrier protein selected from tetanus toxoid, diphtheria toxoid, bovine serum albumin, hen egg lysozyme, gelatin, bovine gamma globulin, B subunit of cholera toxin, B subunit of *E. coli* labile toxin, and flagellin polymer.

7. The cocktail composition of claim 1 wherein the carrier protein is a B subunit of *E. coli* labile toxin.

8. the cocktail composition of claim 4 wherein the carrier protein has one or more C-repeats of a streptococcal M protein.

9. The cocktail composition of claim 4 wherein the carrier protein is a carboxy-terminal half of a streptococcal M protein.

10. The cocktail composition of claim 9 wherein the carboxy-terminal half is of an M5 serotype.

11. The cocktail composition of claim 4 wherein the carrier protein is the carboxy-terminal half of a surface protein from a Gram-positive coccus.

12. The cocktail composition of claim 1 wherein the carrier protein and said at least one amino-terminal peptide fragment of streptococcal M protein are linked in tandem by a linker comprising one or more amino acids.

13. The cocktail composition of claim 12 wherein the amino acids of the linker are encoded by a nucleotide sequence comprising a restriction enzyme site.

14. The cocktail composition of claim 12 wherein the linker ranges in size from 1 amino acid to 30 amino acids.

15. The cocktail composition of claim 12 wherein the linker ranges in size from 2 amino acids to 7 amino acids.

16. The cocktail composition of claim 12 wherein the linker comprises hydrophobic amino acids.

17. The cocktail composition of claim 16 wherein the hydrophobic amino acids are selected from the group consisting of tryptophan, alanine, leucine, isoleucine, valine, tyrosine, phenylalanine, proline, methionine, and combinations thereof.

18. The cocktail composition of claim 12 wherein the linker is proline-rich.

19. The cocktail composition of claim 15 wherein the linker is selected from the group consisting of Ile-Pro-Gly, Pro-Gly-Asn-Pro-Ala-Val-Pro (SEQ ID NO:15), and Asp-Pro-Arg-Val-Pro-Ser-Ser (SEQ ID NO:16).

20. The cocktail composition of claim 18 wherein the linker has two or three prolines and two or three glycines.

21. The cocktail composition of claim 12 wherein the linker is His-Gly or Gly-Ser.

22. The cocktail composition of claim 1 wherein said at least one serotype of Group A streptococcal M protein is serotype M1, M3, M12, M18, or M19.

23. The cocktail composition of claim 12 wherein said at least one serotype of Group A streptococcal M protein is serotype M1, M3, M12, M18, or M19.

24. The cocktail composition of claim 1 wherein said at least one serotype is from rheumatogenic Group A streptococci.

25. The cocktail composition of claim 12 wherein said at least one serotype is from rheumatogenic Group A streptococci.

26. The cocktail composition according to any one of claims 1, 12, 22, and 23 further comprising a biologically acceptable diluent or adjuvant.

27. A method of eliciting opsonic antibodies to at least one Group A streptococcal serotype without eliciting antibodies that cross-react with mammalian tissue antigens, comprising administering to a patient in need thereof an amount of the composition according to claim 1 or claim 12 that is effective in eliciting said opsonic antibodies.

28. A method of eliciting opsonic antibodies to at least one Group A streptococcal serotype without eliciting antibodies that cross-react with mammalian tissue antigens, comprising administering to a patient in need thereof an amount of the cocktail composition according to claim 26 that is effective in eliciting said opsonic antibodies.

29. The method according to claim 27 wherein the composition is administered intracutaneously, intranasally, parenterally, or mucosally.

30. The method according to claim 28 wherein the composition is administered intracutaneously, intranasally, parenterally, or mucosally.

* * * * *

UNITED STATES PATENT AND TRADEMARK OFFICE

CERTIFICATE OF CORRECTION

PATENT NO. : 7,074,416 B2
APPLICATION NO. : 10/141627
DATED : July 11, 2006
INVENTOR(S) : James B. Dale It is certified that error appears in the above-identified patent and that said Letters Patent is hereby corrected as shown below:

Column 29
Line 43, "atreptococcal" should read as --streptococcal--.

Signed and Sealed this

Sixth Day of November, 2007

JON W. DUDAS
*Director of the United States Patent and Trademark Office*

SEQUENCE LISTING

```
<160> NUMBER OF SEQ ID NOS: 19

<210> SEQ ID NO 1
<211> LENGTH: 417
<212> TYPE: DNA
<213> ORGANISM: Artificial Sequence
<220> FEATURE:
<223> OTHER INFORMATION: LT-B-M24 hybrid molecule

<400> SEQUENCE: 1

atgaataaag taaaatgtta tgttttattt acggcgttac tatcctctct atgtgcatac      60

ggagctcccc agtctattac agaactatgt tcggaatatc gcaacacaca aatatatacg     120

ataaatgaca agatactatc atatacggaa tcgatggcag gcaaaagaga aatggttatc     180

attacattta agagcggcgc aacatttcag gtcgaagtcc cgggcagtca acatatagac     240

tcccaaaaaa aagccattga aaggatgaag gacacattaa gaatcacata tctgaccgag     300
```

-continued

```
accaaaattg ataaattatg tgtatggaat aataaaaccc ccaattcaat tgcggcaatc    360

agtatggaaa accatggagt cgcgactagg tctcagacag atactctgga aaaataa       417


<210> SEQ ID NO 2
<211> LENGTH: 138
<212> TYPE: PRT
<213> ORGANISM: Artificial Sequence
<220> FEATURE:
<223> OTHER INFORMATION: LT-B-M24 hybrid molecule

<400> SEQUENCE: 2

Met Asn Lys Val Lys Cys Tyr Val Leu Phe Thr Ala Leu Leu Ser Ser
 1               5                  10                  15

Leu Cys Ala Tyr Gly Ala Pro Gln Ser Ile Thr Glu Leu Cys Ser Glu
            20                  25                  30

Tyr Arg Asn Thr Gln Ile Tyr Thr Ile Asn Asp Lys Ile Leu Ser Tyr
        35                  40                  45

Thr Glu Ser Met Ala Gly Lys Arg Glu Met Val Ile Ile Thr Phe Lys
    50                  55                  60

Ser Gly Ala Thr Phe Gln Val Glu Val Pro Gly Ser Gln His Ile Asp
65                  70                  75                  80

Ser Gln Lys Lys Ala Ile Glu Arg Met Lys Asp Thr Leu Arg Ile Thr
                85                  90                  95

Tyr Leu Thr Glu Thr Lys Ile Asp Lys Leu Cys Val Trp Asn Asn Lys
            100                 105                 110

Thr Pro Asn Ser Ile Ala Ala Ile Ser Met Glu Asn His Gly Val Ala
        115                 120                 125

Thr Arg Ser Gln Thr Asp Thr Leu Glu Lys
    130                 135


<210> SEQ ID NO 3
<211> LENGTH: 765
<212> TYPE: DNA
<213> ORGANISM: Artificial Sequence
<220> FEATURE:
<223> OTHER INFORMATION: An antigen of M5 and a carrier of the
      COOH-terminal portion of M5

<400> SEQUENCE: 3

atggtcgcga ctaggtctca gacagatact ctggaaaaag tacaagaagg atccaacaaa     60

atttcagacg caagccgtaa gggtcttcgt cgtgacttag acgcatcgcg tgaagctaag    120

aagcaattag aagctgaaca ccaaaaactt gaagaacaaa acaagatttc agaagcaagt    180

cgcaaaggcc ttcgccgtga tttagacgca tcacgtgaag ctaagaagca attagaagct    240

gaacaacaaa aacttgaaga acaaaacaag atttcagaag caagtcgcaa aggccttcgc    300

cgtgatttag acgcatcacg tgaagctaag aaacaagttg aaaaagcttt agaagaagca    360

aacagcaaat tagctgctct tgaaaaactt aacaaagagc ttgaagaaag caagaaatta    420

acagaaaaag aaaaagctga gctacaagca aaacttgaag cagaagcaaa agcactcaaa    480

gaacaattag caaaacaagc tgaagaactt gcaaaactaa gagctggaaa agcatcagac    540

tcacaaaccc ctgatacaaa accaggaaac aaagctgttc caggtaaagg tcaagcacca    600

caagcaggta caaaaccaaa ccaaaacaaa gcaccaatga aggaaactaa gagacagtta    660

ccatcaacag gtgaaacagc taacccattc ttcacagcgg cagcccttac tgttatggca    720

acagctggag tagcagcagt tgtaaaacgc aaagaagaaa attaa                    765
```

-continued

```
<210> SEQ ID NO 4
<211> LENGTH: 254
<212> TYPE: PRT
<213> ORGANISM: Artificial Sequence
<220> FEATURE:
<223> OTHER INFORMATION: An antigen of M5 and a carrier of the
      COOH-terminal portion of M5

<400> SEQUENCE: 4

Met Val Ala Thr Arg Ser Gln Thr Asp Thr Leu Glu Lys Val Gln Glu
 1               5                  10                  15

Gly Ser Asn Lys Ile Ser Asp Ala Ser Arg Lys Gly Leu Arg Arg Asp
            20                  25                  30

Leu Asp Ala Ser Arg Glu Ala Lys Lys Gln Leu Glu Ala Glu His Gln
        35                  40                  45

Lys Leu Glu Glu Gln Asn Lys Ile Ser Glu Ala Ser Arg Lys Gly Leu
    50                  55                  60

Arg Arg Asp Leu Asp Ala Ser Arg Glu Ala Lys Lys Gln Leu Glu Ala
65                  70                  75                  80

Glu Gln Gln Lys Leu Glu Glu Gln Asn Lys Ile Ser Glu Ala Ser Arg
                85                  90                  95

Lys Gly Leu Arg Arg Asp Leu Asp Ala Ser Arg Glu Ala Lys Lys Gln
            100                 105                 110

Val Glu Lys Ala Leu Glu Glu Ala Asn Ser Lys Leu Ala Ala Leu Glu
        115                 120                 125

Lys Leu Asn Lys Glu Leu Glu Glu Ser Lys Lys Leu Thr Glu Lys Glu
    130                 135                 140

Lys Ala Glu Leu Gln Ala Lys Leu Glu Ala Glu Ala Lys Ala Leu Lys
145                 150                 155                 160

Glu Gln Leu Ala Lys Gln Ala Glu Glu Leu Ala Lys Leu Arg Ala Gly
                165                 170                 175

Lys Ala Ser Asp Ser Gln Thr Pro Asp Thr Lys Pro Gly Asn Lys Ala
            180                 185                 190

Val Pro Gly Lys Gly Gln Ala Pro Gln Ala Gly Thr Lys Pro Asn Gln
        195                 200                 205

Asn Lys Ala Pro Met Lys Glu Thr Lys Arg Gln Leu Pro Ser Thr Gly
    210                 215                 220

Glu Thr Ala Asn Pro Phe Phe Thr Ala Ala Ala Leu Thr Val Met Ala
225                 230                 235                 240

Thr Ala Gly Val Ala Ala Val Val Lys Arg Lys Glu Glu Asn
                245                 250


<210> SEQ ID NO 5
<211> LENGTH: 855
<212> TYPE: DNA
<213> ORGANISM: Artificial Sequence
<220> FEATURE:
<223> OTHER INFORMATION: An antigen of three segments  of M5 and a
      carrier of the COOH-terminal portion of M5

<400> SEQUENCE: 5

atggtcgcga ctaggtctca gacagatact ctggaaaaag tacaagaagt cgcgactagg      60

tctcagacag atactctgga aaaagtacaa gaagtcgcga ctaggtctca gacagatact     120

ctggaaaaag tacaagaagg attcaacaaa atttcagacg caagccgtaa gggtcttcgt     180

cgtgacttag acgcatcgcg tgaagctaag aagcaattag aagctgaaca ccaaaaacct     240

gaagaacaaa acaagatttc agaagcaagt cgcaaaggcc ttcgccgtga tttagacgca     300
```

-continued

```
tcacgtgaag ctaagaagca attagaagct gaacaacaaa aacttgaaga acaaaacaag    360

atttcagaag caagtcgcaa aggccttcgc cgtgatttag acgcatcacg tgaagctaag    420

aaacaagttg aaaaagcttt agaagaagca aacagcaaat tagctgctct tgaaaaactt    480

aacaaagagc ttgaagaaag caagaaatta acagaaaaag aaaaagctga gctacaagca    540

aaacttgaag cagaagcaaa agcactcaaa gaacaattag caaaacaagc tgaagaactt    600

gcaaaactaa gagctggaaa agcatcagac tcacaaaccc ctgatacaaa accaggaaac    660

aaagctgttc caggtaaagc tcaagcacca caagcaggta caaaaccaaa ccaaaacaaa    720

gcaccaatga aggaaactaa gagacagtta ccatcaacag gtgaaacagc taacccattc    780

ttcacagcgg cagcccttac tgttatggca acagctggag tagcagcagt tgtaaaacgc    840

aaagaagaaa attaa                                                     855


<210> SEQ ID NO 6
<211> LENGTH: 284
<212> TYPE: PRT
<213> ORGANISM: Artificial Sequence
<220> FEATURE:
<223> OTHER INFORMATION: An antigen of three fragments of M5 and a
      carrier of the COOH-terminal portion of M5

<400> SEQUENCE: 6

Met Val Ala Thr Arg Ser Gln Thr Asp Thr Leu Glu Lys Val Gln Glu
 1               5                  10                  15

Val Ala Thr Arg Ser Gln Thr Asp Thr Leu Glu Lys Val Gln Glu Val
            20                  25                  30

Ala Thr Arg Ser Gln Thr Asp Thr Leu Glu Lys Val Gln Glu Gly Phe
        35                  40                  45

Asn Lys Ile Ser Asp Ala Ser Arg Lys Gly Leu Arg Arg Asp Leu Asp
    50                  55                  60

Ala Ser Arg Glu Ala Lys Lys Gln Leu Glu Ala Glu His Gln Lys Pro
65                  70                  75                  80

Glu Glu Gln Asn Lys Ile Ser Glu Ala Ser Arg Lys Gly Leu Arg Arg
                85                  90                  95

Asp Leu Asp Ala Ser Arg Glu Ala Lys Lys Gln Leu Glu Ala Glu Gln
            100                 105                 110

Gln Lys Leu Glu Glu Gln Asn Lys Ile Ser Glu Ala Ser Arg Lys Gly
        115                 120                 125

Leu Arg Arg Asp Leu Asp Ala Ser Arg Glu Ala Lys Lys Gln Val Glu
    130                 135                 140

Lys Ala Leu Glu Glu Ala Asn Ser Lys Leu Ala Ala Leu Glu Lys Leu
145                 150                 155                 160

Asn Lys Glu Leu Glu Glu Ser Lys Lys Leu Thr Glu Lys Glu Lys Ala
                165                 170                 175

Glu Leu Gln Ala Lys Leu Glu Ala Glu Ala Lys Ala Leu Lys Glu Gln
            180                 185                 190

Leu Ala Lys Gln Ala Glu Glu Leu Ala Lys Leu Arg Ala Gly Lys Ala
        195                 200                 205

Ser Asp Ser Gln Thr Pro Asp Thr Lys Pro Gly Asn Lys Ala Val Pro
    210                 215                 220

Gly Lys Ala Gln Ala Pro Gln Ala Gly Thr Lys Pro Asn Gln Asn Lys
225                 230                 235                 240

Ala Pro Met Lys Glu Thr Lys Arg Gln Leu Pro Ser Thr Gly Glu Thr
                245                 250                 255
```

-continued

```
Ala Asn Pro Phe Phe Thr Ala Ala Ala Leu Thr Val Met Ala Thr Ala
            260                 265                 270

Gly Val Ala Ala Val Val Lys Arg Lys Glu Glu Asn
        275                 280
```

<210> SEQ ID NO 7
<211> LENGTH: 15
<212> TYPE: PRT
<213> ORGANISM: Artificial Sequence
<220> FEATURE:
<223> OTHER INFORMATION: NH2-terminal fragment of M protein for constructing antigens, which elicit opsonic antibodies in an immunized animal

<400> SEQUENCE: 7

```
Val Ala Thr Arg Ser Gln Thr Asp Thr Leu Glu Lys Val Gln Glu
 1               5                  10                  15
```

<210> SEQ ID NO 8
<211> LENGTH: 15
<212> TYPE: PRT
<213> ORGANISM: Artificial Sequence
<220> FEATURE:
<223> OTHER INFORMATION: NH2-terminal fragment of M protein for constructing antigens, which elicit opsonic antibodies in an immunized animal

<400> SEQUENCE: 8

```
Ala Val Thr Arg Gly Thr Ile Asn Asp Pro Gln Arg Ala Lys Glu
 1               5                  10                  15
```

<210> SEQ ID NO 9
<211> LENGTH: 15
<212> TYPE: PRT
<213> ORGANISM: Artificial Sequence
<220> FEATURE:
<223> OTHER INFORMATION: NH2-terminal fragment of M protein for constructing antigens, which elicit opsonic antibodies in an immunized animal

<400> SEQUENCE: 9

```
Arg Val Phe Pro Arg Gly Thr Val Glu Asn Pro Asp Lys Ala Arg
 1               5                  10                  15
```

<210> SEQ ID NO 10
<211> LENGTH: 15
<212> TYPE: PRT
<213> ORGANISM: Artificial Sequence
<220> FEATURE:
<223> OTHER INFORMATION: NH2-terminal fragment of M protein for constructing antigens, which elicit opsonic antibodies in an immunized animal

<400> SEQUENCE: 10

```
Arg Val Arg Tyr Thr Arg His Thr Pro Glu Asp Lys Leu Lys Lys
 1               5                  10                  15
```

<210> SEQ ID NO 11
<211> LENGTH: 15
<212> TYPE: PRT
<213> ORGANISM: Artificial Sequence
<220> FEATURE:
<223> OTHER INFORMATION: NH2-terminal fragment of M protein for constructing antigens, which elicit opsonic antibodies in an immunized animal

<400> SEQUENCE: 11

-continued

```
Asp Ala Arg Ser Val Asn Gly Glu Phe Pro Arg His Val Lys Leu
 1               5                  10                  15


<210> SEQ ID NO 12
<211> LENGTH: 15
<212> TYPE: PRT
<213> ORGANISM: Artificial Sequence
<220> FEATURE:
<223> OTHER INFORMATION: NH2-terminal fragment of M protein for
      constructing antigens, which elicit opsonic
      antibodies in an immunized animal

<400> SEQUENCE: 12

Asn Gly Asp Gly Asn Pro Arg Glu Val Ile Glu Asp Leu Ala Ala
 1               5                  10                  15


<210> SEQ ID NO 13
<211> LENGTH: 15
<212> TYPE: PRT
<213> ORGANISM: Artificial Sequence
<220> FEATURE:
<223> OTHER INFORMATION: NH2-terminal fragment of M protein for
      constructing antigens, which elicit opsonic
      antibodies in an immunized animal

<400> SEQUENCE: 13

Ala Pro Leu Thr Arg Ala Thr Ala Asp Asn Lys Asp Glu Leu Ile
 1               5                  10                  15


<210> SEQ ID NO 14
<211> LENGTH: 15
<212> TYPE: PRT
<213> ORGANISM: Artificial Sequence
<220> FEATURE:
<223> OTHER INFORMATION: NH2-terminal fragment of M protein for
      constructing antigens, which elicit opsonic
      antibodies in an immunized animal

<400> SEQUENCE: 14

His Ser Asp Leu Val Ala Glu Lys Glu Arg Leu Glu Asp Leu Gly
 1               5                  10                  15


<210> SEQ ID NO 15
<211> LENGTH: 7
<212> TYPE: PRT
<213> ORGANISM: Artificial Sequence
<220> FEATURE:
<223> OTHER INFORMATION: Proline rich linker for the desired M protein
      that links the carrier and fragment in tandem

<400> SEQUENCE: 15

Pro Gly Asn Pro Ala Val Pro
 1               5


<210> SEQ ID NO 16
<211> LENGTH: 7
<212> TYPE: PRT
<213> ORGANISM: Artificial Sequence
<220> FEATURE:
<223> OTHER INFORMATION: Proline rich  linker for the desired M protein
      that links the carrier and fragment in tandem

<400> SEQUENCE: 16

Asp Pro Arg Val Pro Ser Ser
 1               5


<210> SEQ ID NO 17
<211> LENGTH: 6
```

-continued

```
<212> TYPE: PRT
<213> ORGANISM: Artificial Sequence
<220> FEATURE:
<223> OTHER INFORMATION: Hexapeptide consensus sequence

<400> SEQUENCE: 17

Leu Pro Ser Thr Gly Glu
 1               5


<210> SEQ ID NO 18
<211> LENGTH: 9
<212> TYPE: PRT
<213> ORGANISM: Artificial Sequence
<220> FEATURE:
<223> OTHER INFORMATION: Proline rich linker for the desired M protein
      that links the carrier and fragment in tandem

<400> SEQUENCE: 18

Pro Gly Pro Gly Gly Ala Pro Leu Gly
 1               5


<210> SEQ ID NO 19
<211> LENGTH: 4
<212> TYPE: PRT
<213> ORGANISM: Artificial Sequence
<220> FEATURE:
<223> OTHER INFORMATION: Tetrapeptide

<400> SEQUENCE: 19

Asn Lys Ile Ser
 1
```